US009475882B2

(12) United States Patent
Clemmons et al.

(10) Patent No.: US 9,475,882 B2
(45) Date of Patent: Oct. 25, 2016

(54) ANTAGONISTS OF IAP-SHPS1 INTERACTION

(71) Applicant: The University of North Carolina at Chapel Hill, Chapel Hill, NC (US)

(72) Inventors: David R. Clemmons, Chapel Hill, NC (US); Laura A. Maile, Chapel Hill, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 193 days.

(21) Appl. No.: 14/076,130

(22) Filed: Nov. 8, 2013

(65) Prior Publication Data

US 2014/0141002 A1    May 22, 2014

Related U.S. Application Data

(62) Division of application No. 13/219,276, filed on Aug. 26, 2011, now Pat. No. 8,613,922.

(51) Int. Cl.
*C07K 16/28* (2006.01)
*A61K 39/00* (2006.01)

(52) U.S. Cl.
CPC ....... *C07K 16/2896* (2013.01); *C07K 16/2803* (2013.01); *A61K 2039/505* (2013.01); *C07K 2317/34* (2013.01); *C07K 2317/76* (2013.01)

(58) Field of Classification Search
None
See application file for complete search history.

(56) References Cited

U.S. PATENT DOCUMENTS

| | | | |
|---|---|---|---|
| 4,229,571 A | 10/1980 | Katsunuma | |
| 5,874,231 A | 2/1999 | Sonenberg et al. | |
| 6,753,146 B1 | 6/2004 | Bernstein | |
| 7,261,892 B2 * | 8/2007 | Terrett | C07H 21/04 424/130.1 |
| 7,282,556 B2 | 10/2007 | Parkos | |
| 2003/0049841 A1 | 3/2003 | Short et al. | |
| 2003/0157100 A1 | 8/2003 | Fukushima | |
| 2003/0157577 A1 | 8/2003 | Fukushima | |
| 2008/0107654 A1 | 5/2008 | Kikuchi et al. | |
| 2010/0215640 A1 | 8/2010 | Clemmons et al. | |
| 2012/0039896 A1 | 2/2012 | Clemmons et al. | |

FOREIGN PATENT DOCUMENTS

| | | |
|---|---|---|
| WO | WO 99/40940 | 8/1999 |
| WO | WO 01/48020 | 7/2001 |
| WO | WO 01/48020 A1 | 7/2001 |

OTHER PUBLICATIONS

Maile, L.A., et al. Mol. Endocrinol. 2008;22:1226-1237.*
Clemmons, "Modifying IGF1 Activity: An Approach to Treat Endocrine Disorders, Atherosclerosis and Cancer" *Nature Reviews, Drug Discovery* 6:821-833 (2007).
Dills et al, "Is Insulinlike Growth Factor 1 Associated with Diabetic Retinopathy?" *Diabetes* 39:191-195 (1990).
Simo et al, "Free Insulin Growth Factor-1 and Vascular Endothelial Growth Factor in the Vitreous Fluid of Patients with Proliferative Diabetic Retinopathy" *Am J Ophthamol* 134:376-382 (2002).
Brown et al. "Integrin-Associated Protein: A 50-kD Plasma Membrane Antigen Physically and Functionally Associated with Integrins" *The Journal of Cell Biology* 111(6):2785-2794 (1990).
Griffin et al. al. "A Link Between Diabetes and Atherosclerosis: Glucose Regulates Expression of CD36 at the Level of Translation" *Nature Medicine* 7(7):840-846 (2001).
Ling et al. "Tyrosine Phosphorylation of the β3-Subunit of the αVβ3 Integrin is Required for Membrane Association of the Tyrosine Phosphatase SHP-2 and its Further Recruitment to the Insulin-Like Growth Factor 1 Receptor" *Molecular Endocrinology* 17(9):1824-1833.
Liu et al. "Peptide-Mediated Inhibition of Neutrophil Transmigration by Blocking CD47 Interactions with Signal Regulatory Protein $\alpha^1$" *The Journal of Immunology* 172:2578-2585 (2004).
Liu et al. "Signal Regulatory Protein (SIRα), a Cellular Ligand for CD47, Regulates Neutrophil Transmigration" *Journal of Biological Chemistry* 277(12):10025-10036 (2002).
Striga et al. "Anterlor Uveltis and Diabetes Mellitus" *Diabetologia Croatica* 24-2 (1995) (Abstract Only).
Subramanian et al. "Phylogenetic Divergence of CD47 Interactions with Human Signal Regulatory Protein Alpha Reveals Locus of Species Specificity. Implications for the Binding Site." *Journal of Biological Chemistry* 282(3):1805-1818 (2007).
Tang et al, "Macrophages in Human Epiretinal and Vitreal Membranes in Patients With Proliferative Intraocular Disorders" *Yan Ke Xue Bao* 12(1):28-32 abstract only (1 page).
Mateo V. et al, CD47 Ligation Induces Capase-independent Cell Death in Chronic Lymphocytic Leukemia. Nature Medicine. Nov. 1999, vol. 5, No. 11, pp. 1277-1284.
Deutscher M.P. Guide to Protein Purification. *Methods in Enzymology*, 1990, vol. 182, pp. 688-700.
Andre Vaillette et al., *High Expression of Inhibitory Receptor SHPS-1 and Its Association with Protein-tyrosine Phosphatase SHP-1 in Macrophages*, The Journal of Biological Chemistry, vol. 273, No. 35:22719-22728, Aug. 28, 1998.
Charles Saginario et al., *MFR, a Putative Receptor Mediating the Fusion of Macrophages*, Molecular and Cellular Biology, vol. 18, No. 11:6213-6223, Nov. 1998.
Peihua Jiang et al., *Integrin-assiciated Protein Is a Ligand for the P84 Neural Adhesion Molecule*, The Journal of Biological Chemistry, vol. 274, No. 2: 559-562, Jan. 8, 1999.
Xin Han et al., *CD47, a Ligand for the Macrophage Fusion Receptor, Participates in Macrophage Multinucleation*, The Journal of Biological Chemisry, vol. 275, No. 48:37984-37992. Dec. 1, 2000.

(Continued)

*Primary Examiner* — Gerald R Ewoldt
(74) *Attorney, Agent, or Firm* — Casimir Jones S.C.; Thomas Isenbarger

(57) ABSTRACT

Provided herein is technology relating to antagonists that inhibit, reduce, or minimize the interaction of integrin associated protein (IAP) with Src homology 2 (SH2) domain-containing protein tyrosine phosphatase substrate 1 (SHPS1) and particularly, but not exclusively, to compositions comprising such antagonists and methods of treatment comprising administering such antagonists.

17 Claims, 13 Drawing Sheets

(56) References Cited

OTHER PUBLICATIONS

Malle et al.; "The Association between Ingetrin-associated Protein and SHPS-1 Regulates Insulin-like Growth Factor-l Receptor Signalling In Vascular Smooth Muscle Cells" *Molecular Biology of the Cell* 14 3519-3528 (2003).

Malle et al.; "Integrin-Associated Protein Binding Domain of Thrombospondin-1 Enhances Insulin-Like Growth Factor-l Receptor Signaling In Vascular Smooth Muscle Cells" *Division of Endocrinology, University of North Carolina, Chapel Hill Circulation Research* 925-931 2003).

Moralez et al.; Insulin-Like Growth Factor Binding Protein-5 (IGFBP-5) Interacts With Thrombospondin-1 to Induce Negative Regulatory Effects on IGF-1 Actions *Journal of Cellular Physiology* 203 328-334 (2005).

Brown E J and Frazier W A. Integrin-associated protein (CD47) and Its ligands. Trends in Cell Biology (Mar. 2001), vol. 11, No. 3, pp. 130-135.

Burgess W H et al. Possible dissociation of the heparin-binding and mitogenic activities of heparin-binding (acldlc fibroblast) growth factor-1 from its receptor-binding activities by site-directed mutagenesis of a single lysine residue. Journal of Cell Biology (Nov. 1990), vol. 111, pp. 2129-2138.

Jiang P et al. Integrin-associated protein is a ligand for the P84 neural adhesion molecule. Journal of Biological Chemistry (Jan. 8, 1999), vol. 274, No. 2, pp. 559-562.

Deutscher M P, ed. Methods in Enzymology (1990), vol. 182, pp. 688-700.

Lazar E et al. Transforming growth factor α(alpha): Mutation of aspartic acid 47 and leucine 48 results in different biological activities. Molecular and Cellular Biology (Mar. 1998), vol. 8, No. 3, pp. 1437-1252.

Maile L A et al. The association between Integrin-associated protein and SHPS-1 regulates insulin-like growth factor-l receptor signaling in vascular smooth muscle cells. Molecular Biology of the Cell (Sep. 2003), vol. 14, pp. 3519-3528.

Maile L A and Clemmons D R . Regulation of IGF-l receptor phosphorylation by integrin associated protein and SHPS-1. Growth Hormone and IGF Research (2002), vol. 12, pp. 253-254 ABS89.

Maile L A and Clemmons D R. Regulation of Insulin-like growth factor I receptor dephosphorylation by SHPS-1 and the tyrosine phospatase SHP-2. The Journal of Biological Chemistry (Mar. 15, 2002), vol. 277, No. 11, pp. 8955-8960.

Macaulay V M. Insulin-like growth factors and cancer. British Journal of Cancer (1992), vol. 65, No. 3, pp. 311-320.

Brodt P et al. Inhibition of the type I insulin-like growth factor receptor expression and signaling: novel strategies for antimetastatic therapy. Biochemical Pharmacology (2000), vol. 60, No. 8, pp. 1101-1107.

Vernon-Wilson E F et al. CD47 is a ligand for rat macrophage membrane signal regulatory protein SIRP (OX41) and human SIRPα1. European Journal of Immunology (Aug. 2000), vol. 30, pp. 2130-2137.

Yoshida H et al. Interaction between Src homology 2 domain bearing protein tyrosine phosphatase substrate-1 and CD47 mediates the adhesion of human B lymphocytes to nonactivated endothelial cells. Journal of Immunology (Apr. 1, 2002), vol. 158, No. 7, p. 3213-3220.

Slamon D J et al. Use of chemotherapy plus a monoclonal antibody against HER2 for metastatic breast cancer that overexpresses HER2. The New England Journal of Medicine (Mar. 15, 2001), vol. 344, No. 11, pp. 783-792.

Margolin K et al. Phase Ib trail of intravenous recombinant humanized monoclonal antibody to vascular endothelial growth factor in combination with chemotherapy in patients with advanced cancer: pharmacologic and long-term safety data. Journal of Clinical Oncology (Feb. 1, 2001), vol. 19, No. 3, pp. 851-856.

Bayes-Genis A et al. The insulin-like growth factor axis: a review of atherosclerosis and restenosis. Circulation Research (Feb. 4, 2000), vol. 86, No. 2, pp. 125-130.

Cochran A G, Antagonists of protein-protein interactions. Chemistry & Biology (Apr. 2000), vol. 7, No. 4, pp. R85-R94.

Clemmons D R and Maile L A. Minireview: integral membrane proteins that function coordinately with the insulin-like growth fctor I receptor to regulate intracellular signaling. Endocrinology (May 2003), vol. 144, No. 5, pp. 1664-1670.

Mateo V et al. CD47 ligation induces caspase-independent cell death in chronic lymphocytic leukemia. Nature Medicine (Nov. 1999), vol. 5, No. 112, pp. 1277-1284.

Chung et al. "Thrombospondin Acts via Integrin-associated Protein to Activate the Platelet INtgrin $\alpha_{IIb}\beta_3$" *The Journal of Biological Chemistry* 272(23):14740-14746 (1997).

Chung et al. "Thrombspondin-1 Acts via IAP/CD47 to Synergize With Collagen in α2β1-Mediated Platelet Activation" *Blood* 94(2):642-648 (1999).

Fujimoto et al. "Thrombospondin-bound Integrin-associated Protein (CD47) Physically and Functionally Modifies Integrin $\alpha_{IIb}\beta_3$ by Its Extracellular Domain" *The Journal of Biological Chemistry* 278(29):26655-26665 (2003).

Gao et al. "Integrin-associated Protein Is a Receptor for the C-terminal Domain of Thrombospondin" *The Journal of Biological Chemistry* 271(1):21-24 (1996).

Gao et al. "Thrombospondin Modulates $\alpha_v\beta_3$ Function through Integrin-associated Protein" *The Journal of Cell Biology* 135:534-544 (1996).

Lindberg et al. "Molecular Cloning of Integrin-associated Protein: An Immunoglobulin Family Member with Multiple Membrane-spanning Domains Implicated in $\alpha_v\beta_3$-dependent Ligand Binding" *The Journal of Cell Biology* 123:485-496 (1993).

Lindberg et al. "Integrin-associated Protein Immunoglobulin Domain Is Necessary for Efficient Vitronectin Bead Binding" *The Journal of Cell Biology* 134(5):1313-1322 (1996).

Ueda et al. "CD47-dependent molecular mechanisms of blood outgrowth endothelial cell attachment on cholesterol-modified polyurethane" *Biomaterials* 31:6394-6399 (2010).

Chao at al. "Anti-CD417 Antibody Synergizes with Rituximab to Promote Phagocytosis and Eradicate Non-Hodgkin Lymphoma" *Cell* 142:699-713 (2010).

Florian et al. "Evaluation of normal and neoplastic human mast cells for expression of CD172a (SIRPα), CD47, and SHP-1" *Journal of Leukocyte Biology* 77:984-992 (2005).

Maile et al. "Insulin-like Growth Factor I Increases $\alpha_v\beta_3$ Affinity by Increasing the Amount of Integrin-associated Protein That Is Associated with Non-raft Domains of the Cellular Membrane" *The Journal of Biological Chemistry* 277(3):1800-1805 (2002).

Subramanian et al. "Species- and cell type-specific interactions between CD47 and human SIRPα" *Blood* 107(6):2548-2556 (2006).

* cited by examiner

ANTAGONISTS OF IAP-SHPS1 INTERACTION

PRIORITY STATEMENT

The present application is a divisional application of, and claims priority to, U.S. application Ser. No. 13/219,276, which has a filing date of Aug. 26, 2011, now U.S. Pat. No. 8,613,922, the entire contents of which are incorporated herein by reference.

STATEMENT OF GOVERNMENT SUPPORT

This invention was made with government support under Grant Nos. AG002331, HL056850, and HG002647 awarded by the National Institutes of Health. The government has certain rights in the invention.

FIELD OF THE INVENTION

The present invention concerns methods for inhibiting IGF-1 activity in subjects in need thereof, such as subjects afflicted with cancer, atherosclerosis, diabetic neuropathy, or retinopathy.

BACKGROUND OF THE INVENTION

Insulin-like growth factor-1 is required for generalized somatic growth, that is the normal growth and development that occurs throughout childhood requires IGF-1. If the IGF-1 gene is deleted from mice, the mice are born at half of a normal size and grow poorly after birth reaching approximately 30% of normal adult size. Therefore this growth factor is an important mitogen for all known cell types.

Interest has emerged in inhibiting IGF-1 activation of mitogenesis in cells because it has been shown that high concentrations of IGF-1 are linked to the development of cancer whereas low concentrations of IGF-1 appear to be cancer protective. For example, U.S. Pat. No. 6,340,674 to Baserga et al. describes an antisense method of inhibiting proliferation of cancer cells by contacting the cancer cells with an oligonucleotide substantially complementary to a region of IGF-1 receptor RNA and which specifically hybridizes to IGF-1 receptor RNA.

In addition, IGF-1 is synthesized in the local microenvironment in several diseases that involve abnormal cellular repair. An important disease of this type is atherosclerosis, which is the leading cause of death in the United States. Cells in the atherosclerotic lesion synthesize excess IGF-1 and therefore excess IGF-1 signaling leads to enlargement of lesions. Several studies have shown that if the effect of this IGF-1 is inhibited, lesion progression is retarded. Therefore there is significant interest in inhibiting IGF-1 action in vessel wall cell types such as smooth muscle cells.

Traditional approaches to inhibiting IGF-1 such as blocking ligand binding to the IGF-1 receptor have failed for two reasons: first, the binding site is quite large and therefore it is difficult to design compounds that will effectively inhibit binding; second, there is a significant structural overlap between the IGF-1 receptor and the insulin receptor, and approaches that have attempted to alter IGF-1 receptor activity by blocking the activity of the receptor have invariably led to toxicity due to coinhibition of the insulin receptor. Antisense techniques present the problem of delivering the active agent to the interior of target cells. Thus there is a need for new ways to inhibit IGF-1 activity or production in cells of subjects in need of such treatment.

SUMMARY OF THE INVENTION

In general, the present invention provides a method of inhibiting cellular activation by insulin-like growth factor-1 (IGF-1) in a subject in need thereof (for example, subjects afflicted with cancer or tumors, atherosclerosis, diabetic neuropathy or retinopathy). The method comprises administering an antagonist that inhibits the binding of IAP to SHPS-1 to the subject in an amount effective to inhibit cellular activation by IGF-1 (for example, an amount effective to treat the said condition or a treatment effective amount).

A more particular aspect of the present invention is a method of treating a tumor in a subject in need thereof, comprising administering to the subject an IAP to SHPS-1 binding antagonist in an amount effective to treat the tumor (e.g., an amount effective to inhibit the effect of IGF-1 on the tumor). Examples of tumors which may be treated include but are not limited to breast cancer tumors, colon cancer tumors, lung cancer tumors, and prostate cancer tumors. Tumors to be treated are those that express IGF-1 receptors.

Another aspect of the present invention is, in a method of treating a tumor in a subject in need thereof by administering a treatment effective amount of an antineoplastic compound (i.e., a chemotherapeutic agent) or radiation therapy to the subject, the improvement comprising administering to the subject an IAP to SHPS-1 binding antagonist in an amount effective to inhibit IGF-1 mediated rescue of tumor cells (that is, inhibit the anti-apoptotic effect of IGF-1 on tumor cells).

A further aspect of the present invention is a method of treating atherosclerosis in a subject in need thereof, comprising administering to the subject an IAP to SHPS-1 binding antagonist in an amount effective to treat the atherosclerosis. Any type of atherosclerotic lesion may be treated, such as coronary atherosclerosis. In general, atherosclerotic lesions to be treated are those in which the lesion cells express IGF-1 receptors.

A further aspect of the present invention is a method of treating diabetic neuropathy in a subject in need thereof, comprising administering to the subject an IAP to SHPS-1 binding antagonist in an amount effective to treat the diabetic neuropathy.

A further aspect of the present invention is a method of treating retinopathy (e.g., diabetic retinopathy) in a subject in need thereof, comprising administering to the subject an IAP to SHPS-1 binding antagonist in an amount effective to treat the retinopathy.

Antagonists that may be used in carrying out the methods described herein, sometimes referred to as active agents herein, may be of any suitable type, including proteins or peptides, such as antibodies. Particular examples of antagonists that can be used to carry out the present invention include but are not limited to antibodies that antagonize IAP to SHPS-1 binding, SHPS-1 fragments comprising, consisting of or consisting essentially of the IAP binding domain, IAP fragments comprising, consisting of or consisting essentially of the SHPS-1 binding domain, analogs thereof, and/or non-peptide mimetics or analogs thereof. In one embodiment of this invention, the antibody can be the monoclonal antibody B6H12.

A further aspect of the present invention is a pharmaceutical formulation comprising an active agent as described herein in a pharmaceutically acceptable carrier.

A further aspect of the present invention is the use of an active agent as described herein for the manufacture of a medicament for carrying out a method of treatment as described herein.

A further aspect of the present invention is an in vitro method of screening compounds for activity in (i) inhibiting cellular activation by insulin-like growth factor-1 (for example, inhibiting cell growth by IGF-1, (ii) treating cancers or tumors (as described above), and/or (iii) treating atherosclerosis (as described above), the method comprising the steps of: (a) adding or contacting a test compound to an in vitro system comprising the SHPS-1 protein and the IAP protein; then (b) determining whether the test compound is an antagonist of IAP to SHPS-1 binding; and then (c) identifying the test compound as active or potentially active in (i) inhibiting cellular activation by insulin-like growth factor-1, (ii) treating cancers or tumors, and/or (iii) treating atherosclerosis when the test compound is an antagonist of IAP to SHPS-1 binding.

The present invention also provides a monoclonal antibody that specifically binds an epitope within amino acids 71-80 of the human IAP protein and is an antagonist of IAP to SHPS-1 binding. A further characteristic of the antibody is that it does not disrupt IAP binding to a $\beta_3$ protein.

The monoclonal antibody described above can be the monoclonal antibody produced by a hybridoma deposited with the American Type Culture Collection (ATCC) on Aug. 17, 2012, and assigned accession number PTA-13161, or a monoclonal antibody that competes for binding to the same epitope as the epitope bound by a monoclonal antibody produced by the hybridoma deposited with the American Type Culture Collection (ATCC) on Aug. 17, 2012, and assigned accession number PTA-13161.

Additionally provided herein is a method of inhibiting IGF-1 actions in a subject in need thereof, comprising administering to the subject the antibody of this invention.

Further provided is a method of treating diabetic retinopathy, diabetic atherosclerosis, diabetic nephropathy and/or coronary artery disease in a subject (e.g. a subject in need thereof), comprising administering to the subject an effective amount of the antibody of this invention. In such methods the antibody can be administered by subcutaneous injection and/or intravenous infusion.

The present invention is explained in greater detail in the following non-limiting Examples.

DETAILED DESCRIPTION OF THE INVENTION

Figure 1:
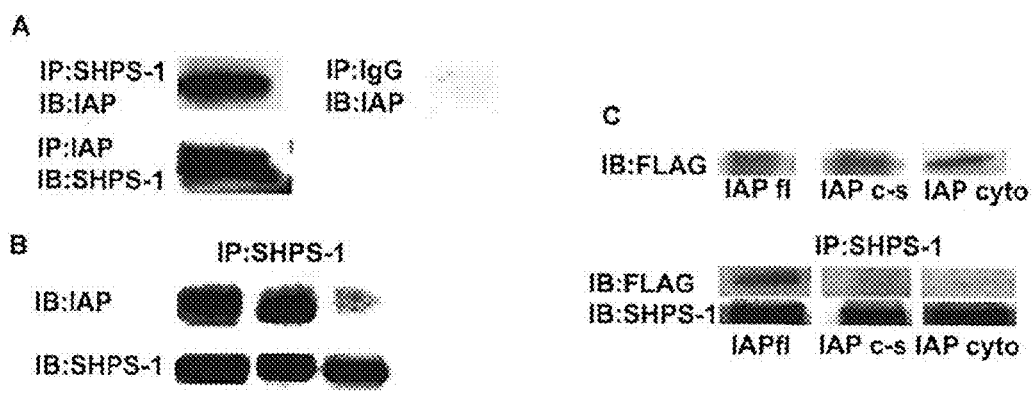
FIGS. 1A-C. Co-precipitation of IAP with SHPS-1 and disruption with anti-IAP antibody. A. Cell lysates were immunoprecipitated with an anti IAP antibody and co-precipitation of SHPS-1 determined by immunoblotting with anti SHPS-1 antiserum or immunoprecipitated with SHPS-1 and co-precipitation of IAP determined by immunblotting with an anti IAP antibody. As a control cell lysates were also immunoprecipitated with an irrelevant polyclonal antibody (IgG) and immunoblotted with an anti IAP antibody. B. Quiescent pSMCs were incubated for two hours±the addition of the anti IAP monoclonal antibody, B6H12 or an irrelevant control monoclonal antibody (both at 4 µg/ml). Co-precipitation of IAP with SHPS-1 was then determined by immunoprecipitating with an SHPS-1 antibody and immunoblotting with an anti IAP antibody. The amount of SHPS-1 protein in each lane is shown in the lower panel. C. Expression of FLAG labeled IAP and association with SHPS-1. Top panel: Expression of FLAG labeled IAP was determined by immunblotting whole cell lysates from cells transfected with each of the IAP cDNA constructs using an anti FLAG antibody. The results as scanning units are: Lane 1:38018, Lane 2:39274, Lane 3:46779. Lower panels: Cell lysates were immunoprecipitated with an anti-SHPS-1 antibody then co-precipitation of FLAG labeled IAP was determined by immunoblotting with an anti FLAG antibody. The amount of SHPS-1 that was immunoprecipitated in each lane is shown in the lower panel.

The present invention is explained in greater detail below. This description is not intended to be a detailed catalog of all the different ways in which the invention may be implemented, or all the features that may be added to the instant invention. For example, features illustrated with respect to one embodiment may be incorporated into other embodiments, and features illustrated with respect to a particular embodiment may be deleted from that embodiment. In addition, numerous variations and additions to the various embodiments suggested herein will be apparent to those skilled in the art in light of the instant disclosure which do not depart from the instant invention. Hence, the following specification is intended to illustrate some particular embodiments of the invention, and not to exhaustively specify all permutations, combinations and variations thereof.

Subjects that may be treated by the present invention include both human subjects for medical purposes and animal subjects for veterinary and drug screening and development purposes. Other suitable animal subjects are, in general, mammalian subjects such as primates, bovines, ovines, caprines, porcines, equines, felines, canines, lagomorphs, rodents (e.g., rats and mice), etc. Human subjects are the most preferred. Human subjects include fetal, neonatal, infant, juvenile and adult subjects.

"IGF-1" as used herein means insulin-like growth factor-1.

"IFG-1R" as used herein means the IGF-1 receptor.

"IAP" as used herein means integrin associated protein. IAP may be of any type but is preferably mammalian IAP (e.g., mouse, rat, rabbit, monkey, pig, etc.), and is most preferably human IAP. IAP (sometimes also called CD47) is known and described in, for example, E. Brown et al., *J Cell*

Biol 111, 2785-94 (1990); C. Rosales et al., *J Immunol* 149, 2759-64 (1992); D. Cooper et al., *Proc Natl Acad Sci USA* 92, 3978-82 (1995)); P. Jiang et al., *J Biol Chem* 274, 559-62 (1999); P. Oldenborg et al., *Science* 288, 2051-4 (2000); M. Seiffert et al., *Blood* 94, 3633-43 (1999); E. Vernon-Wilson et al., *Eur J Immunol* 30, 2130-2137 (2000); H. Yoshida et al., *J Immunol* 168, 3213-20 (2002); and I. Babic et al., *J Immunol* 164, 3652-8 (2000).

"SHPS-1" as used herein means src homology 2 domain containing protein tyrosine phosphatase substrate 1. SHPS-1 may be of any type but is preferably mammalian SHPS-1 (e.g., mouse, rat, rabbit, monkey, pig, etc.), and is most preferably human SHPS-1. SHPS-1 (sometimes also called P84) is known and described in, for example, T. Noguchi et al., *J Biol Chem* 271, 27652-8 (1996); Y. Fujioka et al., *Mol Cell Biol* 16, 6887-99 (1996); A. Kharitonenkov et al., *Nature* 386, 181-6 (1997); M. Stofega et al., *J Biol Chem* 273, 7112-7 (1998); and T. Takada et al., *J Biol Chem* 273, 9234-42 (1998).

"SHP-2" as used herein means src homology 2 containing protein tyrosine phosphatase-2.

"Treat" as used herein refers to any type of treatment or prevention that imparts a benefit to a subject afflicted with a disease or at risk of developing the disease, including improvement in the condition of the subject (e.g., in one or more symptoms), delay in the progression of the disease, delay the onset of symptoms or slow the progression of symptoms, etc. As such, the term "treatment" also includes prophylactic treatment of the subject to prevent the onset of symptoms. As used herein, "treatment" and "prevention" are not necessarily meant to imply cure or complete abolition of symptoms." to any type of treatment that imparts a benefit to a patient afflicted with a disease, including improvement in the condition of the patient (e.g., in one or more symptoms), delay in the progression of the disease, etc.

"Treatment effective amount", "amount effective to treat", or the like as used herein means an amount of the inventive antagonist sufficient to produce a desirable effect upon a patient inflicted with cancer, tumors, atherosclerosis, retinopathy, diabetic neuropathy, or other undesirable medical condition in which IGF-1 is inducing abnormal cellular growth. This includes improvement in the condition of the patient (e.g., in one or more symptoms), delay in the progression of the disease, etc.

"Pharmaceutically acceptable" as used herein means that the compound or composition is suitable for administration to a subject to achieve the treatments described herein, without unduly deleterious side effects in light of the severity of the disease and necessity of the treatment.

Applicants specifically intend that all United States patent references and publications, international patent publications and non-patent references cited herein be incorporated herein by reference in their entirety.

A. Antibodies.

The term "antibodies" as used herein refers to all types of immunoglobulins, including IgG, IgM, IgA, IgD, and IgE. The term "immunoglobulin" includes the subtypes of these immunoglobulins, such as $IgG_1$, $IgG_2$, $IgG_3$, $IgG_4$, etc. Of these immunoglobulins, IgM and IgG are preferred, and IgG is particularly preferred. The antibodies may be of any species of origin, including (for example) mouse, rat, rabbit, horse, or human, or may be chimeric antibodies. See, e.g., M. Walker et al., *Molec. Immunol.* 26, 403-11 (1989). Such monoclonal antibodies are produced in accordance with known techniques. The term "antibody" as used herein includes antibody fragments which retain the capability of binding to a target antigen, for example, Fab, F(ab')$_2$, and Fv fragments, and the corresponding fragments obtained from antibodies other than IgG. Such fragments are also produced by known techniques.

Monoclonal antibodies may be recombinant monoclonal antibodies produced according to the methods disclosed in Reading U.S. Pat. No. 4,474,893, or Cabilly et al., U.S. Pat. No. 4,816,567. The antibodies may also be chemically constructed by specific antibodies made according to the method disclosed in Segel et al., U.S. Pat. No. 4,676,980 (Applicants specifically intend that the disclosure of all U.S. patent references cited herein be incorporated herein by reference in their entirety).

Monoclonal antibodies may be chimeric or "humanized" antibodies produced in accordance with known techniques. For example, chimeric monoclonal antibodies may be complementarily determining region-grafted antibodies (or "CDR-grafted antibodies") produced in accordance with known techniques.

An example of an antibody of this invention is monoclonal antibody B6H12.2 (ATCC Accession No. HB-9771).

The present invention additionally provides a monoclonal antibody produced by a hybridoma cell line deposited with the American Type Culture Collection (ATCC) on Aug. 17, 2012, and assigned accession number PTA-13161. This hybridoma was produced according to standard protocols for monoclonal antibody production as are well known in the art. The immunogen administered to the mice was the peptide ALNKSTVPTDC (SEQ ID NO: 15), which represents amino acid residues 71-80 of the human IAP amino acid sequence as provided herein (i.e., ALNKSTVPTD (SEQ ID NO: 16)), with a cysteine residue added at the carboxyl terminus that was used to link the peptide to KLH. Therefore, the actual immunogen was a conjugate of the active peptide and KLH, linked by a cysteine. Mice were immunized and then the spleens were harvested for fusion with myeloma cells. The myeloma cell supernatants were screened by ELISA using the immunogen linked to BSA to coat the plates. The positive supernatants were then re-cloned four separate times before the final clone producing the high affinity antibody was selected. The numbering of the amino acids for human IAP is based on the reference amino acid sequence of GenBank® Database Accession No. NP_942088 (SEQ ID NO: 6) (incorporated by reference herein) and is as follows, with the first amino acid numbered 1 and the last amino acid numbered 305. Amino acid residues 71-80 are bolded in the sequence below.

```
MWPLVAALLL GSACCGSAQL LFNKTKSVEF TFCNDTVVIP

CFVTNMEAQN TTEVYVKWKF KGRDIYTFDG ALNKSTVPTD

FSSAKIEVSQ LLKGDASLKM DKSDAVSHTG NYTCEVTELT

REGETIIELK YRVVSWFSPN ENILIVIFPI FAILLFWGQF

GIKTLKYRSG GMDEKTIALL VAGLVITVIVIV GAILFVPG

EYSLKNATGL GLIVTSTGIL ILLHYYVFST AIGLTSFVIA

ILVIQVIAYI LAVVGLSLCI AACIPMHGPL LISGLSILAL

AQLLGLVYMK FVASNQKTIQ PPRNN.
```

In some embodiments, the antibody is (a) the monoclonal antibody produced by the hybridoma deposited with the ATCC and assigned accession number PTA-13161, or (b) a monoclonal antibody that competes for binding to the same epitope as the epitope bound by a monoclonal antibody produced by the hybridoma deposited with the ATCC and assigned accession number PTA-13161 (i.e., a monoclonal antibody that specifically binds to the epitope bound by a monoclonal antibody produced by the hybridoma deposited with the ATCC and assigned accession number PTA-13161).

The monoclonal antibody having ATCC accession number PTA-13161 binds to the human IAP protein and disrupts IAP binding to SHPS-1 without disrupting IAP binding to $\beta_3$ protein. The $\beta_3$ integrin subunit is a component of the $\alpha_V\beta_3$ integrin. It is expressed abundantly on the surface of vascular endothelial cells. Agents which disrupt the function of $\alpha_V\beta_3$ integrin have been shown to lead to changes in endothelial cell function as well as inhibition of endothelial cell growth. Furthermore since this integrin subunit is expressed on platelets, agents that have been shown to inhibit its function in platelets have been shown to stimulate platelet aggregation, which can lead to thrombosis. This is an important distinguishing feature of this monoclonal antibody. Many antibodies that react with human IAP also bind to $\alpha_V\beta_3$ integrin. Disrupting IAP binding to $\beta_3$ could lead to side effects, making the therapeutic use of such antibodies undesirable. The monoclonal antibody having ATCC accession number PTA-13161 has the unexpected benefit of binding to human IAP and disrupting its association with SHPS-1 without disrupting IAP binding to $\beta_3$.

Further provided herein is a humanized monoclonal antibody having ATCC accession number PTA-13161. The humanized form of the antibody is prepared using in vitro mutagenesis. The CD-R regions will be left intact unless it is necessary to alter single amino acids with these regions to avoid immunogenicity. Similarly, the framework regions will be scanned for regions that might confer immunogenicity and that appropriate mouse amino acid residues will be changed to human amino acid residues. The immunogenicity of the entire antibody will then be determined using lymphocytes prepared from human HLA donors from each of the 20 HLA haplotypes.

Monoclonal Fab fragments may be produced in *Escherichia coli* by recombinant techniques known to those skilled in the art. See, e.g., W. Huse, *Science* 246, 1275-81 (1989).

Antibodies for use in the present invention specifically bind to their target with a relatively high binding affinity, for example, with a dissociation constant of about $10^{-6}$ or $10^{-8}$ up to $10^{-12}$ or $10^{-13}$.

Humanized monoclonal antibodies that are antagonists of IAP to SHPS-1 binding are a further aspect of the present invention. A humanized antibody of the present invention may be produced from antibodies as described herein by any suitable technique, using a conventional complementarity determining region (CDR)-grafting method as disclosed in EPO Publication No. 0239400 and U.S. Pat. Nos. 6,407,213; 6,180,370; and 5,693,762, all of which are incorporated herein by reference in their entirety. Alternatively, a humanized antibody may be produced by directly modifying antibody variable regions without diminishing the native affinity of the domain for antigen while reducing its immunogenicity with respect to a heterologous species (see, e.g., U.S. Pat. No. 5,766,886 which is incorporated herein by reference in its entirety).

Using a CDR-grafting method, the humanized antibody is generally produced by combining a human framework region (FR) with one or more CDR's from a non-human (usually a mouse or rat) immunoglobulin which are capable of binding to a predetermined antigen.

Typically, the humanized antibody comprises substantially all of at least one, and typically two, variable domains (Fab, Fab', F(ab')$_2$, Fabc, Fv) in which all or substantially all of the CDR correspond to those of a non-human immunoglobulin and all or substantially all of the FR are those of a human immunoglobulin consensus sequence. The humanized antibody optimally also comprises at least a portion of an immunoglobulin constant region (Fc), typically that of a human immunoglobulin. Ordinarily, the antibody contains both the light chain as well as at least the variable domain of a heavy chain. The antibody also may include the CH1, hinge, CH2, CH3, and CH4 regions of the heavy chain.

The humanized antibody may be selected from any class of immunoglobulins, including IgM, IgG, IgD, IgA and IgE, and any isotype, including IgG$_1$, IgG$_2$, IgG$_3$ and IgG$_4$. Usually the constant domain is a complement fixing constant domain where it is desired that the humanized antibody exhibit cytotoxic activity, and the class is typically IgG$_1$. Where such cytotoxic activity is not desirable, the constant domain may be of the IgG$_2$ class. The humanized antibody may comprise sequences from more than one class or isotype, and selecting particular constant domains to optimize desired effector functions is within the ordinary skill in the art.

The FR and CDR of the humanized antibody need not correspond precisely to the parental sequences, however, it is preferable that substitutions, insertions or deletions not be extensive. Usually, at least 75% of the humanized antibody residues should correspond to those of the parental FR and CDR sequences, more often 90%, and most preferably greater than 95%.

The term "antibody" or "antibodies" as used herein refers to all types of immunoglobulins, including IgG, IgM, IgA, IgD, and IgE. The antibody can be monoclonal or polyclonal and can be of any species of origin, including (for example) mouse, rat, rabbit, horse, goat, sheep, camel, or human, or can be a chimeric antibody. See, e.g., Walker et al., *Molec. Immunol.* 26:403 (1989). The antibodies can be recombinant monoclonal antibodies produced according to the methods disclosed in U.S. Pat. No. 4,474,893 or U.S. Pat. No. 4,816,567. The antibodies can also be chemically constructed according to the method disclosed in U.S. Pat. No. 4,676,980.

Antibody fragments included within the scope of the present invention include, for example, Fab, Fab', F(ab')$_2$, and Fv fragments; domain antibodies, diabodies; vaccibodies, linear antibodies; single-chain antibody molecules; and multispecific antibodies formed from antibody fragments. Such fragments can be produced by known techniques. For example, F(ab')$_2$ fragments can be produced by pepsin digestion of the antibody molecule, and Fab fragments can be generated by reducing the disulfide bridges of the F(ab')$_2$ fragments. Alternatively, Fab expression libraries can be constructed to allow rapid and easy identification of monoclonal Fab fragments with the desired specificity (Huse et al., *Science* 254:1275 (1989)).

Antibodies of the invention may be altered or mutated for compatibility with species other than the species in which the antibody was produced. For example, antibodies may be humanized or camelized. Humanized forms of non-human (e.g., murine) antibodies are chimeric immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. Humanized antibodies include human immunoglobulins (recipient antibody) in which residues from a complementarity determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the framework (FR) regions (i.e., the sequences between the CDR regions) are those of a human immunoglobulin consensus sequence. The humanized antibody optimally also will comprise at least a portion of an immunoglobulin constant region (Fc), typically that of a human immunoglobulin (Jones et al., *Nature* 321:522 (1986); Riechmann et al., *Nature,* 332:323 (1988); and Presta, *Curr. Op. Struct. Biol.* 2:593 (1992)).

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can essentially be performed following the method of Winter and co-workers (Jones et al., *Nature* 321:522 (1986); Riechmann et al., *Nature* 332:323 (1988); Verhoeyen et al., *Science* 239:1534 (1988)), by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues (e.g., all of the CDRs or a portion thereof) and possibly some FR residues are substituted by residues from analogous sites in rodent antibodies.

Human antibodies can also be produced using various techniques known in the art, including phage display libraries (Hoogenboom and Winter, *J. Mol. Biol.* 227:381 (1991); Marks et al., *J. Mol. Biol.* 222:581 (1991)). The techniques of Cole et al. and Boerner et al. are also available for the preparation of human monoclonal antibodies (Cole et al., Monoclonal Antibodies and Cancer Therapy, Alan R. Liss, p. 77 (1985) and Boerner et al., *J. Immunol.* 147:86 (1991)). Similarly, human antibodies can be made by introducing human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in the following scientific publications: Marks et al., *Bio/Technology* 10:779 (1992); Lonberg et al., *Nature* 368:856 (1994); *Morrison, Nature* 368:812 (1994); Fishwild et al., *Nature Biotechnol.* 14:845 (1996); Neuberger, *Nature Biotechnol.* 14:826 (1996); Lonberg and Huszar, *Intern. Rev. Immunol.* 13:65 (1995).

Polyclonal antibodies used to carry out the present invention can be produced by immunizing a suitable animal (e.g., rabbit, goat, etc.) with an antigen to which a monoclonal antibody to the target binds, collecting immune serum from the animal, and separating the polyclonal antibodies from the immune serum, in accordance with known procedures.

Monoclonal antibodies used to carry out the present invention can be produced in a hybridoma cell line according to the technique of Kohler and Milstein, *Nature* 265:495 (1975). For example, a solution containing the appropriate antigen can be injected into a mouse and, after a sufficient time, the mouse sacrificed and spleen cells obtained. The spleen cells are then immortalized by fusing them with myeloma cells or with lymphoma cells, typically in the presence of polyethylene glycol, to produce hybridoma cells. The hybridoma cells are then grown in a suitable medium and the supernatant screened for monoclonal antibodies having the desired specificity. Monoclonal Fab fragments can be produced in *E. coli* by recombinant techniques known to those skilled in the art. See, e.g., Huse, *Science* 246:1275 (1989).

Antibodies specific to the target polypeptide can also be obtained by phage display techniques known in the art.

Various immunoassays can be used for screening to identify antibodies having the desired specificity for the polypeptides of this invention. Numerous protocols for competitive binding or immunoradiometric assays using either polyclonal or monoclonal antibodies with established specificity are well known in the art. Such immunoassays typically involve the measurement of complex formation between an antigen and its specific antibody (e.g., antigen/antibody complex formation). A two-site, monoclonal-based immunoassay utilizing monoclonal antibodies reactive to two non-interfering epitopes on the polypeptides or peptides of this invention can be used as well as a competitive binding assay.

Antibodies can be conjugated to a solid support (e.g., beads, plates, slides or wells formed from materials such as latex or polystyrene) in accordance with known techniques. Antibodies can likewise be conjugated to detectable groups such as radiolabels (e.g., $^{35}S$, $^{125}I$, $^{131}I$), enzyme labels (e.g., horseradish peroxidase, alkaline phosphatase), and fluorescence labels (e.g., fluorescein) in accordance with known techniques. Determination of the formation of an antibody/antigen complex in the methods of this invention can be by detection of, for example, precipitation, agglutination, flocculation, radioactivity, color development or change, fluorescence, luminescence, etc., as is well known in the art.

In various embodiments, the antibody of this invention is an antibody or a fragment thereof (e.g., a monoclonal antibody) that specifically binds to IAP. In some embodiments, the antibody of this invention is an antibody or a fragment thereof (e.g., a monoclonal antibody) that specifically binds to SHPS-1.

In one embodiment, the antibody is a monoclonal antibody produced by a hybridoma cell line deposited with the ATCC on Aug. 17, 2012, and assigned accession number PTA-13161. In a further embodiment, the antibody is a monoclonal antibody or a fragment thereof that competes for binding to the same epitope specifically bound by the monoclonal antibody produced by the hybridoma cell line deposited with the ATCC on Aug. 17, 2012, and assigned accession number PTA-13161. In another embodiment, the antibody is a monoclonal antibody or a fragment thereof that specifically binds to the same epitope specifically bound by the monoclonal antibody produced by the hybridoma cell line deposited with the ATCC on Aug. 17, 2012, and assigned accession number PTA-13161. In certain embodiments, the monoclonal antibody or a fragment thereof is a chimeric antibody or a humanized antibody. In additional embodiments, the chimeric or humanized antibody comprises at least a portion of the CDRs of the monoclonal antibody produced by the hybridoma cell line deposited with the ATCC on Aug. 17, 2012, and assigned accession number PTA-13161. As used herein, a "portion" of a CDR is defined as one or more of the three loops from each of the light and heavy chain that make up the CDRs (e.g., from 1-6 of the CDRs) or one or more portions of a loop comprising, consisting essentially of, or consisting of at least three contiguous amino acids. For example, the chimeric or humanized antibody may comprise 1, 2, 3, 4, 5, or 6 CDR loops, portions of 1, 2, 3, 4, 5, or 6 CDR loops, or a mixture thereof.

B. Protein/Peptide Antagonists and Other Antagonists.

The amino terminal Ig domain of IAP and the extracellular Ig variable domain of SHPS-1 are sufficient for their physical interaction, and these regions may serve as protein or peptide antagonists of IAP to SHPS-1 binding. Thus, a further aspect of the present invention is an active agent that is a protein or peptide comprising, consisting of, or consisting essentially of the SHPS-1 binding domain of IAP (e.g., an IAP fragment; the amino terminal Ig domain of IAP). Specific examples include, but are not limited to, a polypeptide consisting of amino acids 1 to 140 of mouse IAP; a polypeptide consisting of amino acids 1 to 135 of mouse IAP; a polypeptide consisting of amino acids 5 to 135 of mouse IAP; a polypeptide consisting of amino acids 5 to 95 of mouse IAP; a polypeptide consisting of amino acids 19 to 95 of mouse IAP; a polypeptide consisting of amino acids 1 to 140 of mouse IAP; a polypeptide consisting of amino acids 1 to 135 of rat IAP; a polypeptide consisting of amino acids 5 to 135 of rat IAP; a peptide consisting of amino acids 5 to 95 of rat IAP; a polypeptide consisting of amino acids 19 to 95 of rat IAP; a peptide consisting of amino acids 1 to 10, 1 to 15, 1 to 20, 1 to 25, 1 to 30, 1 to 35, 1 to 40, 1 to 50, 1 to 60, 1 to 70, 1 to 80, 1 to 90, 1 to 100, 1 to 110, 1 to 120, 1 to 130, 1 to 135 and/or 1 to 140 of human IAP; a peptide consisting of amino acids 5 to 15, 5 to 20, 5 to 25, 5 to 30, 5 to 35, 5 to 40, 5 to 45, 5 to 50, 5 to 60, 5 to 70, 5 to 80, 5 to 95, 5 to 100, 5 to 110, 5 to 120, and/or 5 to 135 of human IAP; a peptide consisting of 10 to 20, 10 to 30, 10 to 35, 10 to 40, 10 to 45, 10 to 50, 10 to 60, 10 to 70, 10 to 80, 10 to 95, 10 to 100, 10 to 110, 10 to 120, and/or 10 to 135 of human IAP; a peptide consisting of amino acids 19 to 30, 19 to 35, 19 to 40, 19 to 45, 19 to 50, 19 to 60, 19 to 70, 19 to 80, 19 to 95, 19 to 100, 19 to 110, 19 to 120, and/or 19 to 135 of human IAP, and a peptide consisting of amino acids 30 to 50, 30 to 60, 30 to 70, 30 to 80, 30 to 90, 40 to 50, 40 to 60, 40 to 70, 40 to 80, 40 to 90, 40 to 100, 50 to 60, 50 to 70, 50 to 60, 60 to 70, 60 to 80, 70 to 80, 80 to 90, 70 to 90, 50 to 80, 50 to 90 and/or 50 to 100 of human IAP. Also provided herein are antibodies of this invention, which specifically bind any of the IAP peptides and/or epitopes within any of the IAP peptides described herein.

Mouse, human and rat IAP are all known as described above and numbering herein refers to standard numbering assigned to amino acid residues in the full length proteins. The numbering of the amino acids for human IAP is based on the reference amino acid sequence of GenBank® Database Accession No. NP_942088 (SEQ ID NO: 6, incorporated by reference herein) and is as follows, with the first amino acid numbered 1 and the last amino acid numbered 305:

```
MWPLVAALLL GSACCGSAQL LFNKTKSVEF TFCNDTVVIP

CFVTNMEAQN TTEVYVKWKF KGRDIYTFDG ALNKSTVPTD

FSSAKIEVSQ LLKGDASLKM DKSDAVSHTG NYTCEVTELT

REGETIIELK YRVVSWFSPN ENILIVIFPI FAILLFWGQF

GIKTLKYRSG GMDEKTIALL VAGLVITVIVIV GAILFVPG
```

-continued
```
EYSLKNATGL GLIVTSTGIL ILLHYYVFST AIGLTSFVIA

ILVIQVIAYI LAVVGLSLCI AACIPMHGPL LISGLSILAL

AQLLGLVYMK FVASNQKTIQ PPRNN.
```

In some embodiments, the IAP peptide can comprise, consist essentially of or consist of a peptide having the amino acid sequence FVTNMEAQNTTEVYKWK (SEQ ID NO: 7, aa 42-59), a peptide having the amino acid sequence KWKFKGRDIYTFDGALNK (SEQ ID NO: 8, aa 57-74), a peptide having the amino acid sequence STVPTDFSSAKIEVSQLLKGD (SEQ ID NO: 9, aa 75-95), a peptide having the amino acid sequence YTFDGALNKSTVPTDFS (SEQ ID NO: 10, aa 66-92), and any combination thereof.

A still further aspect of the present invention is an active agent that is a protein or peptide comprising, consisting of, or consisting essentially of the IAP binding domain of SHPS-1 (e.g., an SHPS-1 fragment; the extracellular Ig variable domain of SHPS-1).

Specific examples include, but are not limited to, a polypeptide consisting of amino acids 1 to 160 of mouse SHPS-1; a polypeptide consisting of amino acids 5 to 150 of mouse SHPS-1; a polypeptide consisting of amino acids 29 to 150 of mouse SHPS-1; a polypeptide consisting of amino acids 1 to 160 of rat SHPS-1; a polypeptide consisting of amino acids 5 to 150 of rat SHPS-1; a polypeptide consisting of amino acids 29 to 150 of rat SHPS-1; a peptide consisting of amino acids 1 to 10, 1 to 15, 1 to 20, 1 to 25, 1 to 30, 1 to 35, 1 to 40, 1 to 50, 1 to 60, 1 to 70, 1 to 80, 1 to 90, 1 to 100, 1 to 110, 1 to 120, 1 to 130, 1 to 135 and/or 1 to 140 of human SHPS-1; a peptide consisting of amino acids 5 to 15, 5 to 20, 5 to 25, 5 to 30, 5 to 35, 5 to 40, 5 to 45, 5 to 50, 5 to 60, 5 to 70, 5 to 80, 5 to 95, 5 to 100, 5 to 110, 5 to 120, and/or 5 to 135 of human SHPS-1; a peptide consisting of 10 to 20, 10 to 30, 10 to 35, 10 to 40, 10 to 45, 10 to 50, 10 to 60, 10 to 70, 10 to 80, 10 to 95, 10 to 100, 10 to 110, 10 to 120, and/or 10 to 135 of human SHPS-1; a peptide consisting of amino acids 19 to 30, 19 to 35, 19 to 40, 19 to 45, 19 to 50, 19 to 60, 19 to 70, 19 to 80, 19 to 95, 19 to 100, 19 to 110, 19 to 120, and/or 19 to 135 of human SHPS-1, a peptide consisting of amino acids 30 to 50, 30 to 60, 30 to 70, 30 to 80, 30 to 90, 40 to 50, 40 to 60, 40 to 70, 40 to 80, 40 to 90, 40 to 100, 50 to 60, 50 to 70, 50 to 80, 50 to 90 and/or 50 to 100 of human SHPS-1, and a peptide consisting of amino acids 100 to 120, 100 to 130, 100 to 140, 100 to 150, 120 to 140, 120 to 130, 120 to 150, 130 to 140 and/or 130 to 150 of human SHPS-1. Also provided herein are antibodies of this invention, which specifically bind any of the SHPS-1 peptides and/or epitopes within any of the SHPS-1 peptides described herein.

Mouse, human and rat SHPS-1 are all known as described above and numbering herein refers to standard numbering assigned to amino acid residues in the full length proteins. The numbering of the amino acids for human SHPS-1 is based on the reference amino acid sequence of GenBank® Database Accession No. BAA12974 (SEQ ID NO: 11, incorporated by reference herein) and is as follows, with the first amino acid numbered 1 and the last amino acid numbered 503:

```
MEPAGPAPGR LGPLLCLLLA ASCAWSGVAG EEELQVIQPD

KSVSVAAGES AILHCTVTSL IPVGPIQWFR GAGPARELIY

NQKEGHFPRV TTVSESTKRE NMDFSISISN ITPADAGTYY
```

```
CVKFRKGSPD TEFKSGAGTE LSVRAKPSAP VVSGPAARAT

PQHTVSFTCE SHGFSPRDIT LKWFKNGNEL SDFQTNVDPV

GESVSYSIHS TAKVVLTRED VHSQVICEVA HVTLQGDPLR

GTANLSETIR VPPTLEVTQQ PVRAENQVNV TCQVRKFYPQ

RLQLTWLENG NVSRTETAST VTENKDGTYN WMSWLLVNVS

AHRDDVKLTC QVEHDGQPAV SKSHDLKVSA HPKEQGSNTA

AENTGSNERN IYIVVGVVCT LLVALLMAAL YLVRIRQKKA

QGSTSSTRLH EPEKNAREIT QDTNDITYAD LNLPKGKKPA

PQAAEPNNHT EYASIQTSPQ PASEDTLTYA DLDMVHLNRT

PKQPAPKPEP SFSEYASVQV PRK.
```

In some embodiments, the SHPS-1 peptide can comprise, consist essentially of, or consist of a peptide having the amino acid sequence RELIYNQKEGHFPRVTTVS (SEQ ID NO: 12, aa 76-93), a peptide having the amino acid sequence VTSLIPVGPIQWFRG (SEQ ID NO: 13, aa 57-71), a peptide having the amino acid sequence VKFRK-GSP (SEQ ID NO: 14, aa 122-129), and any combination thereof.

IAP and SHPS-1 fragments that may serve as active agents include analogs thereof. An "analog" is a chemical compound similar in structure to a first compound, and having either a similar or opposite physiologic action as the first compound. With particular reference to the present invention, peptide analogs are those compounds which, while not having the amino acid sequences of the corresponding protein or peptide, are capable of antagonizing IAP to SHPS-1 binding. Such analogs may be peptide or non-peptide analogs, including but not limited to nucleic acid analogs, as described in further detail below.

In protein or peptide molecules which interact with a receptor (e.g., on IAP or SHPS-1), the interaction between the protein or peptide and the receptor generally takes place at surface-accessible sites in a stable three-dimensional molecule. By arranging the critical binding site residues in an appropriate conformation, peptides analogs which mimic the essential surface features of the peptides described herein may be generated and synthesized in accordance with known techniques. Methods for determining peptide three-dimensional structure and analogs thereto are known, and are sometimes referred to as "rational drug design techniques". See, e.g., U.S. Pat. No. 4,833,092 to Geysen; U.S. Pat. No. 4,859,765 to Nestor; U.S. Pat. No. 4,853,871 to Pantoliano; U.S. Pat. No. 4,863,857 to Blalock; (applicants specifically intend that the disclosures of all U.S. Patent references cited herein be incorporated by reference herein in their entirety). See also Waldrop, Science 247, 28029 (1990); Rossmann, Nature 333, 392 (1988); Weis et al., Nature 333, 426 (1988); James et al., Science 260, 1937 (1993) (development of benzodiazepine peptidomimetic compounds based on the structure and function of tetrapeptide ligands).

In general, those skilled in the art will appreciate that minor deletions or substitutions may be made to the amino acid sequences of proteins or peptides of the present invention without unduly adversely affecting the activity thereof. Thus, peptides containing such deletions or substitutions are a further aspect of the present invention. In peptides containing substitutions or replacements of amino acids, one or more amino acids of a peptide sequence may be replaced by one or more other amino acids wherein such replacement does not affect the function of that sequence. Such changes can be guided by known similarities between amino acids in physical features such as charge density, hydrophobicity/hydrophilicity, size and configuration, so that amino acids are substituted with other amino acids having essentially the same functional properties. For example: Ala may be replaced with Val or Ser; Val may be replaced with Ala, Leu, Met, or Ile, preferably Ala or Leu; Leu may be replaced with Ala, Val or Ile, preferably Val or Ile; Gly may be replaced with Pro or Cys, preferably Pro; Pro may be replaced with Gly, Cys, Ser, or Met, preferably Gly, Cys, or Ser; Cys may be replaced with Gly, Pro, Ser, or Met, preferably Pro or Met; Met may be replaced with Pro or Cys, preferably Cys; His may be replaced with Phe or Gln, preferably Phe; Phe may be replaced with His, Tyr, or Trp, preferably His or Tyr; Tyr may be replaced with His, Phe or Trp, preferably Phe or Trp; Trp may be replaced with Phe or Tyr, preferably Tyr; Asn may be replaced with Gln or Ser, preferably Gln; Gln may be replaced with His, Lys, Glu, Asn, or Ser, preferably Asn or Ser; Ser may be replaced with Gln, Thr, Pro, Cys or Ala; Thr may be replaced with Gln or Ser, preferably Ser; Lys may be replaced with Gln or Arg; Arg may be replaced with Lys, Asp or Glu, preferably Lys or Asp; Asp may be replaced with Lys, Arg, or Glu, preferably Arg or Glu; and Glu may be replaced with Arg or Asp, preferably Asp. Once made, changes can be routinely screened to determine their effects on function with enzymes.

Non-peptide mimetics of the proteins or peptides of the present invention (i.e., non-peptide IAP to SHPS-1 binding antagonists) are also an aspect of this invention. Non-protein mimetics may be generated in accordance with known techniques such as using computer graphic modeling to design non-peptide, organic molecules able to antagonize IAP to SHPS-1 binding. See, e.g., Knight, BIO/Technology 8, 105 (1990); Itzstein et al, Nature 363, 418 (1993) (peptidomimetic inhibitors of influenza virus enzyme, sialidase). Itzstein et al., Nature 363, 418 (1993), modeled the crystal structure of the sialidase receptor protein using data from x-ray crystallography studies and developed an inhibitor that would attach to active sites of the model; the use of nuclear magnetic resonance (NMR) data for modeling is also known in the art and such techniques may be utilized in carrying out the instant invention. See also Lam et al., Science 263, 380 (1994) regarding the rational design of bioavailable nonpeptide cyclic ureas that function as HIV protease inhibitors. Lam et al. used information from x-ray crystal structure studies of HIV protease inhibitor complexes to design non-peptide inhibitors.

Analogs or antagonists may also be developed by utilizing high-throughput screening of compound libraries, as discussed in further detail below. Note that such compound libraries may be fully random libraries, or libraries generated and/or selected based upon the information based upon the antibody active agents, IAP fragment active agents, or SHPS-1 fragment active agents as described above.

Antagonists or analogs of the foregoing that may be used to carry out the invention may also be developed by generating a library of molecules, selecting for those molecules which act as antagonists, and identifying and amplifying the selected antagonists. See, e.g., Kohl et al., Science 260, 1934 (1993) (synthesis and screening of tetrapeptides for inhibitors of farnesyl protein transferase, to inhibit ras oncoprotein dependent cell transformation). Eldred, et al, (J. Med Chem. 37:3882 (1994)) describe nonpeptide antagonists that mimic the Arg-Gly-Asp sequence. Likewise, Ku, et al, (J. Med Chem. 38:9 (1995)) further illustrate the synthesis of a series of such compounds. Techniques for constructing and screening combinatorial libraries of oligomeric biomolecules to identify those that specifically bind to a given receptor protein are known. Suitable oligomers include peptides, oligonucleotides, carbohydrates, nonoligonucleotides (e.g., phosphorothioate oligonucleotides; see Chem. and Engineering News, page 20, Feb. 7, 1994) and nonpeptide polymers (see, e.g., "peptoids" of Simon et al., Proc. Natl. Acad. Sci. USA 89, 9367 (1992)). See also U.S. Pat. No. 5,270,170 to Schatz; Scott and Smith, Science 249, 386-390 (1990); Devlin et al., Science 249, 404406 (1990); Edgington, BIO/Technology 11, 285 (1993). Peptide libraries may be synthesized on solid supports, or expressed on the surface of bacteriophage viruses (phage display libraries). Known screening methods may be used by those skilled in the art to screen combinatorial libraries to identify antagonists. Techniques are known in the art for screening synthesized molecules to select those with the desired activity, and for labeling the members of the library so that selected active molecules may be identified. See, e.g., Brenner and Lerner, Proc. Natl. Acad. Sci. USA 89, 5381 (1992) (use of genetic tag to label molecules in a combinatorial library); PCT US93/06948 to Berger et al., (use of recombinant cell transformed with viral transactivating element to screen for potential antiviral molecules able to inhibit initiation of viral transcription); Simon et al., Proc. Natl. Acad. Sci. USA 89, 9367 (1992) (generation and screening of "peptoids", oligomeric N-substituted glycines, to identify ligands for biological receptors); U.S. Pat. No. 5,283,173 to Fields et al., (use of genetically altered *Saccharomyces cerevisiae* to screen peptides for interactions).

As used herein, "combinatorial library" refers to collections of diverse oligomeric biomolecules of differing sequence, which can be screened simultaneously for activity as a ligand for a particular target. Combinatorial libraries may also be referred to as "shape libraries", i.e., a population of randomized polymers which are potential ligands. The shape of a molecule refers to those features of a molecule that govern its interactions with other molecules, including Van der Waals, hydrophobic, electrostatic and dynamic. Screening procedures that may be used in conjunction with such libraries are discussed in greater detail below.

C. Formulations and Administration.

For administration, the active agent will generally be mixed, prior to administration, with a non-toxic, pharmaceutically acceptable carrier substance (e.g. normal saline or phosphate-buffered saline), and will be administered using any medically appropriate procedure, e.g., parenteral administration (e.g., injection) such as by intravenous or intraarterial injection. In some embodiments, administration can be by injection into the eye (e.g., intraocular, intraretinal and/or intravisceral injection). In some embodiments, administration can be by injection directly into the site of treatment, e.g., directly into a tumor. In some embodiments the active agent of this invention can be linked or conjugated to a carrier (e.g., polyethylene glycol) to alter the half-life or other properties of the active agent.

The active agents described above may be formulated for administration in a pharmaceutical carrier in accordance with known techniques. See, e.g., Remington, *The Science And Practice of Pharmacy* (9$^{th}$ Ed. 1995). In the manufacture of a pharmaceutical formulation according to the invention, the active compound (including the physiologically acceptable salts thereof) is typically admixed with, inter alia, an acceptable carrier. The carrier must, of course, be acceptable in the sense of being compatible with any other ingredients in the formulation and must not be deleterious to the patient. The carrier may be a liquid and is preferably formulated with the compound as a unit-dose formulation which may contain from 0.01 or 0.5% to 95% or 99% by weight of the active compound.

Formulations of the present invention suitable for parenteral administration comprise sterile aqueous and non-aqueous injection solutions of the active compound, which preparations are preferably isotonic with the blood of the intended recipient. These preparations may contain antioxidants, buffers, bacteriostats and solutes which render the formulation isotonic with the blood of the intended recipient.

The active agents may be administered by any medically appropriate procedure, e.g., normal intravenous or intraarterial administration. In certain cases, direct administration to an atherosclerotic vessel may be desired.

Active agents may be provided in lyophylized form in a sterile aseptic container or may be provided in a pharmaceutical formulation in combination with a pharmaceutically acceptable carrier, such as sterile pyrogen-free water or sterile pyrogen-free physiological saline solution.

Dosage of the active agent will depend, among other things, on the condition of the subject, the particular category or type of cancer being treated, the route of administration, the nature of the therapeutic agent employed, and the sensitivity of the tumor to the particular therapeutic agent. For example, the dosage will typically be about 1 to 10 micrograms per kilogram subject body weight. The specific dosage of the antibody is not critical, as long as it is effective to result in some beneficial effects in some individuals within an affected population. In general, the dosage may be as low as about 1, 5, 10, 20 or 50 micrograms per kilogram subject body weight, or lower, and as high as about 200, 500, 1000, 2000 or 5000 micrograms per kilogram subject body weight, or even higher.

The active agents of the present invention may optionally be administered in conjunction with other, different, cytotoxic agents such as chemotherapeutic or antineoplastic compounds or radiation therapy useful in the treatment of the disorders or conditions described herein (e.g., chemotherapeutics or antineoplastic compounds). The other compounds may be administered concurrently. As used herein, the word "concurrently" means sufficiently close in time to produce a combined effect (that is, concurrently may be simultaneously, or it may be two or more administrations occurring before or after each other) As used herein, the phrase "radiation therapy" includes, but is not limited to, x-rays or gamma rays which are delivered from either an externally applied source such as a beam or by implantation of small radioactive sources. Examples of other suitable chemotherapeutic agents which may be concurrently administered with active agents as described herein include, but are not limited to, Alkylating agents (including, without limitation, nitrogen mustards, ethylenimine derivatives, alkyl sulfonates, nitrosoureas and triazenes): Uracil mustard, Chlormethine, Cyclophosphamide (Cytoxan™), Ifosfamide, Melphalan, Chlorambucil, Pipobroman, Triethylenemelamine, Triethylenethiophosphoramine, Busulfan, Carmustine, Lomustine, Streptozocin, Dacarbazine, and Temozolomide; Antimetabolites (including, without limitation, folic acid antagonists, pyrimidine analogs, purine analogs and adenosine deaminase inhibitors): Methotrexate, 5-Fluorouracil, Floxuridine, Cytarabine, 6-Mercaptopurine, 6-Thioguanine, Fludarabine phosphate, Pentostatine, and Gemcitabine; Natural products and their derivatives (for example, vinca alkaloids, antitumor antibiotics, enzymes, lymphokines and epipodophyllotoxins): Vinblastine, Vincristine, Vindesine, Bleomycin, Dactinomycin, Daunorubicin, Doxorubicin, Epirubicin, Idarubicin, Ara-C, paclitaxel (paclitaxel is commercially available as Taxol®), Mithramycin, Deoxyco-formycin, Mitomycin-C, L-Asparaginase, Interferons (especially IFN-a), Etoposide, and Teniposide; Other anti-proliferative cytotoxic agents are navelbene, CPT-11, anastrazole, letrazole, capecitabine, reloxafine, cyclophosphamide, ifosamide, and droloxafine. Additional anti-proliferative cytotoxic agents include, but are not limited to, melphalan, hexamethyl melamine, thiotepa, cytarabin, idatrexate, trimetrexate, dacarbazine, L-asparaginase, camptothecin, topotecan, bicalutamide, flutamide, leuprolide, pyridobenzoindole derivatives, interferons, and interleukins. Preferred classes of antiproliferative cytotoxic agents are the EGFR inhibitors, Her-2 inhibitors, CDK inhibitors, and Herceptin® (trastuzumab). (see, e.g., U.S. Pat. No. 6,537,988; U.S. Pat. No. 6,420,377). Such compounds may be given in accordance with techniques currently known for the administration thereof.

D. Screening Procedures.

As noted above, the present invention provides screening procedures which may be utilized alone or in combination with information on the various active agents described above to generate still additional active agents.

For example, active agents may also be developed by generating a library of molecules, selecting for those molecules which act as ligands for a specified target, and identifying and amplifying the selected ligands. See, e.g., Kohl et al., Science 260, 1934 (1993) (synthesis and screening of tetrapeptides for inhibitors of farnesyl protein transferase, to inhibit ras oncoprotein dependent cell transformation). Techniques for constructing and screening combinatorial libraries of oligomeric biomolecules to identify those that specifically bind to a given receptor protein are known. Suitable oligomers include peptides, oligonucleotides, carbohydrates, nonoligonucleotides (e.g., phosphorothioate oligonucleotides; see Chem. and Engineering News, page 20, 7 Feb. 1994) and nonpeptide polymers (see, e.g., "peptoids" of Simon et al., Proc. Natl. Acad. Sci. USA 89, 9367 (1992)). See also U.S. Pat. No. 5,270,170 to Schatz; Scott and Smith, Science 249, 386-390 (1990); Devlin et al., Science 249, 404-406 (1990); Edgington, BIO/Technology 11, 285 (1993). Peptide libraries may be synthesized on solid supports, or expressed on the surface of bacteriophage viruses (phage display libraries). Known screening methods may be used by those skilled in the art to screen combinatorial libraries to identify compounds that antagonize IAP to SHPS-1 binding. Techniques are known in the art for screening synthesized molecules to select those with the desired activity, and for labeling the members of the library so that selected active molecules may be identified. See, e.g., Brenner and Lerner, Proc. Natl. Acad. Sci. USA 89, 5381 (1992) (use of genetic tag to label molecules in a combinatorial library); PCT US93/06948 to Berger et al., (use of recombinant cell transformed with viral transactivating element to screen for potential antiviral molecules able to inhibit initiation of viral transcription); Simon et al., Proc. Natl. Acad. Sci. USA 89, 9367 (1992) (generation and screening of "peptoids", oligomeric N-substituted glycines, to identify ligands for biological receptors); U.S. Pat. No. 5,283,173 to Fields et al., (use of genetically altered Saccharomyces cerevisiae to screen peptides for interactions).

As used herein, "combinatorial library" refers to collections of diverse oligomeric biomolecules of differing sequence, which can be screened simultaneously for activity as a ligand for a particular target. Combinatorial libraries may also be referred to as "shape libraries", i.e., a population of randomized polymers which are potential ligands. The shape of a molecule refers to those features of a molecule that govern its interactions with other molecules, including Van der Waals, hydrophobic, electrostatic and dynamic.

Nucleic acid molecules may also act as ligands for receptor proteins. See, e.g., Edgington, BIO/Technology 11, 285 (1993). U.S. Pat. No. 5,270,163 to Gold and Tuerk describes a method for identifying nucleic acid ligands for a given target molecule by selecting from a library of RNA molecules with randomized sequences those molecules that bind specifically to the target molecule. A method for the in vitro selection of RNA molecules immunologically cross-reactive with a specific peptide is disclosed in Tsai, Kenan and Keene, Proc. Natl. Acad. Sci. USA 89, 8864 (1992) and Tsai and Keene, J. Immunology 150, 1137 (1993). In the method, an antiserum raised against a peptide is used to select RNA molecules from a library of RNA molecules; selected RNA molecules and the peptide compete for antibody binding, indicating that the RNA epitope functions as a specific inhibitor of the antibody-antigen interaction.

As noted above, potential active agents or candidate compounds as described can be readily screened for activity in (i) inhibiting cellular activation by insulin-like growth factor-1 (for example, inhibiting cell growth by IGF-1), (ii) treating cancers or tumors (as described above), and/or (iii) treating atherosclerosis (as described above) and/or diabetic neuropathy and/or retinopathy and/or any other undesirable disorder characterized by IGF-1 induced cell proliferation. The method comprises the steps of: (a) adding or contacting a test compound to an in vitro system comprising the SHPS-1 protein and the IAP protein (this term including binding fragments thereof sufficient to bind to the other); then (b) determining whether the test compound is an antagonist of IAP to SHPS-1 binding; and then (c) identifying the test compound as active or potentially active in (i) inhibiting cellular activation by insulin-like growth factor-1, (ii) treating cancers or tumors, and/or (iii) treating atherosclerosis (or other disorder characterized by IGF-1 induced cell proliferation) when the test compound is an antagonist of IAP to SHPS-1 binding. The in vitro system may be in any suitable format, such as cells that express both the SHPS-1 protein and the IAP protein. In the alternative, the in vitro system may be a cell-free system, such as an aqueous preparation of SHPS-1 and IAP, or the binding fragments thereof. The contacting, determining and identifying steps may be carried out in any suitable manner, such as manually, semi-automated, or by a high throughput screening apparatus. The determining step may be carried out by any suitable technique, such as by precipitation, by labeling one of the fragments with a detectable group such as a radioactive group, etc., all of which may be carried out in accordance with procedures well known to those skilled in the art.

The present invention is explained in greater detail in the following non-limiting Examples, in which the following abbreviations are used: Dulbecco's modified medium (DMEM-H), Fetal bovine serum (FBS), insulin-like growth factor-1 (IGF-1), IGF-1 receptor (IGF-1R), immunoglobulin (Ig), integrin associated protein (IAP), serum free medium (SFM), smooth muscle cells (SMCs), Src homology 2 domain-containing protein tyrosine phosphatase substrate 1 (SHPS-1), Src homology 2 domain-containing protein tyrosine phosphatase 2 (SHP-2).

EXAMPLE 1

The Association Between Integrin Associated Protein and SHPS-1 Regulates IGF-1 Receptor Signaling in Vascular Smooth Muscle Cells Insulin-like growth factor-1 (IGF-1) is a potent stimulator of smooth muscle cell (SMC) migration and proliferation (J.

Jones et al., *Proc Natl Acad Sci USA* 93, 2482-7 (1996)). There is increasing evidence to show that the ability of IGF-1 to initiate intracellular signaling is regulated not only by its association with its own transmembrane receptor but also by other transmembrane proteins such as the αVβ3 integrin (B. Zheng and D. Clemmons, *Proc Natl Acad Sci USA* 95, 11217-22 (1998); L. Maile and D. Clemmons, *J Biol Chem* 277, 8955-60 (2002)), integrin associated protein (IAP (L. Maile et al., *J Biol Chem* 277, 1800-5 (2002))) and Src homology 2 domain containing protein tyrosine phosphatase substrate-1 (SHPS-1) (Maile and Clemmons, supra).

SHPS-1 was identified as a tyrosine phosphorylated protein that binds to SHP-2 in v-SRC transformed fibroblasts (T. Noguchi et al., *J Biol Chem* 271, 27652-8 (1996)) and in insulin stimulated chinese hamster ovary cells (Y. Fujioka et al., *Mol Cell Biol* 16, 6887-99 (1996)). The cytoplasmic region of SHPS-1 contains 2 immunoreceptor tyrosine based inhibitory motifs (A. Kharitonenkov et al., *Nature* 386, 181-6 (1997)) that are phosphorylated in response to various mitogenic stimuli (see, e.g., M. Stofega et al., *J Biol Chem* 273, 7112-7 (1998)) and integrin mediated cell attachment (see, e.g., T. Takada et al., *J Biol Chem* 273, 9234-42 (1998)). This phosphorylation generates binding sites for the recruitment and activation of Src homology 2 domain tyrosine phosphatase (SHP-2) that in turn dephosphorylates SHPS-1.

In stably attached smooth muscle cells (SMCs) SHP-2 is localized to a site close to the cell membrane from where it is transferred to the SHPS-1 following IGF-1 stimulated SHPS-1 phosphorylation (L. Maile and D. Clemmons, *J Biol Chem* 277, 8955-60 (2002)). This recruitment of SHP-2 is followed by the dephosphorylation of SHPS-1 and the transfer of SHP-2 to the IGF-1R where it subsequently dephosphorylates this substrate. The importance of SHPS-1 phosphorylation in regulating IGF-1R dephosphorylation is demonstrated in cells expressing a truncated form of SHPS-1 in which the SHP-2 binding sites have been deleted. In these cells transfer of SHP-2 to both SHPS-1 and the IGF-1R is blocked and sustained phosphorylation of both molecules is evident.

IAP was first identified by its ability to associate with αVβ3 (E. Brown et al., *J Cell Biol* 111, 2785-94 (1990)) and to increase the affinity of the integrin for its ligands (E. Brown et al., *J Cell Biol* 111, 2785-94 (1990)). IAP consists of a N-terminal (extracellular) Ig variable type domain followed by five membrane spanning hydrophobic helices and a cytoplasmic tail (C. Rosales et al., *J Immunol* 149, 2759-64 (1992); D. Cooper et al., *Proc Natl Acad Sci USA* 92, 3978-82 (1995)).

IAP has been shown to bind to SHPS-1 (P. Jiang et al., *J Biol Chem* 274, 559-62 (1999); P. Oldenborg et al., *Science* 288, 2051-4 (2000); M. Seiffert et al., *Blood* 94, 3633-43 (1999); E. Vernon-Wilson et al., *Eur J Immunol* 30, 2130-2137 (2000); H. Yoshida et al., *J Immunol* 168, 3213-20 (2002); I. Babic et al., *J Immunol* 164, 3652-8 (2000)). The amino terminal Ig domain of IAP and the extracellular Ig variable domain of SHPS-1 are sufficient for their physical interaction. The effect of IAP binding to SHPS-1 on growth factor stimulated SHPS-1 phosphorylation and SHP-2 recruitment has not been reported. The aim of these studies was to determine the effect of IAP association with SHPS-1 on IGF-1 stimulated SHPS-1 phosphorylation and subsequent SHP-2 recruitment and to study how this alters IGF-1R dependent SMC actions.

A. Experimental Procedures.

Human IGF-1 was a gift from Genentech (South San Francisco, Calif., USA); Polyvinyl difluoride membrane (IMMOBILON P™) was purchased from Millipore Corporation (Bedford, Mass., USA). Autoradiographic film was obtained from Eastman Kodak (Rochester, N.Y., USA). Fetal Bovine Serum, Dulbecco's modified medium, penicillin and streptomycin were purchased from Life Technologies, (Grand Island, N.Y., USA). The IGF-1R β chain antibody and the monoclonal phosphotyrosine antibody (PY99) were purchased from Santa Cruz (Santa Cruz, Calif., USA). The polyclonal SHP-2 and SHPS-1 antibodies were purchased from Transduction Laboratories (Lexington, Ky., USA). The monoclonal antibody against IAP, B6H12, was purified from a B cell hybrid purchased from the American Type Culture Collection, Rockville, Md., USA, and the anti FLAG monoclonal antibody was purchased from Sigma Chemical Company (St Louis, Mo., USA). The antibody against the dual phosphorylated (active) form of p42/p44 MAP kinase (MAPK) and the antibody against total p42/p44 MAPK protein were purchased from Cell Signaling Technology (Beverley, Mass., USA). All other reagents were purchased from Sigma Chemical Company (St Louis, Mo., USA) unless otherwise stated.

Porcine aortic SMCs (pSMCs) were isolated as previously described (A. Gockerman et al., *Endocrinology* 136, 4168-73 (1995)) and maintained in Dulbecco's modified medium supplemented with glucose (4.5 gm/liter), penicillin (100 units/ml), streptomycin (100 µg/ml) (DMEM-H) and 10% Fetal Bovine serum (FBS) in 10 cm tissue culture plates (Falcon Laboratory, Franklin Lakes N.J., USA). The cells were used between passage 5 and 16.

B. Generation of Expression Vectors

Full-Length Porcine IAP with a C-Terminal FLAG Epitope (IAPfl).

Full-length porcine IAP was cloned by RT-PCR from a cDNA library that had been derived from pSMCs that had been isolated as previously described (A. Gockerman et al., *Endocrinology* 136, 4168-73 (1995)). The 5' primer sequence 5' ATGTGGCCCTGGTGGTC ((SEQ ID NO: 1) corresponded to nucleotides 121-139 of the porcine sequence. The 3' primer sequence was complementary to nucleotides 1005-1030 with the addition of bases encoding the FLAG sequence (underlined) and a stop codon. The sequence was:

(SEQ ID NO: 2)
5' TCA<u>TTTGTCGTCGTCGTCTTTGTAGTC</u>GGTTGTATAGTCT 3'.

Following sequencing, the cDNA was cloned into the pcDNA V5 his 3.1 vector (Invitrogen, Carlsbad, Calif., USA).

IAP with Truncation of Extracellular Domain at Residue 135 and Containing a C-Terminal FLAG Epitope (IAPcyto).

The pcDNA V5 his 3.1 vector containing the IAPfl cDNA sequence was linearized and the mutant form of IAP was generated using PCR with a 5' oligonucleotide encoding bases 527-556 (5' TCTCCAAATGAAAAATCCTCATTGT-TATT 3') (SEQ ID NO: 3) and the same 3' oligonucleotide that was used to generate the IAPfl. The PCR product was cloned in to pcDNA V5 his 3.1.

IAP in which Cysteine 33 and 261 are Substituted with Serine Residues Containing a C-Terminal FLAG Epitope (IAPc-s).

The IAPfl cDNA was subcloned in a pRcRSV expression vector and it was used as a template to perform single stranded mutagenesis to incorporate the two substitutions. The pRcRSV vector contains a neomycin derivative (G418) resistance gene and a bacteriophage origin of replication (F1) gene that permits direct single stranded mutagenesis of the cDNA. Two oligonucleotides encoding the base substitutions were used. They were: C33S: complementary to nucleotides 204-225 except for a base substitution to encode a serine (underlined) 5' GTAACAGTTGTATTG GAAACGGTGAATTCTA 3' ((SEQ ID NO: 4) and C261S: complementary to nucleotides 888-918 except for the base substitution to encode the serine residue (underlined):

(SEQ ID NO: 5)
5' CCATGCACTGGGGTAGACTCTGAGACGCAG 3'.

Following sequencing the DNA constructs were subcloned into pMEP4 expression vector (Invitrogen, Carlsbad, Calif., USA).

Transfection of pSMCs.

Cells that had been grown to 70% confluency were transfected with one of three IAP cDNA constructs as previously described (24). Hygromycin resistant pSMCs were selected and maintained in DMEM-H containing 15% FBS and 100 µg/ml hygromycin as described previously (Y. Imai et al., *J Clin Invest* 100, 2596-605 (1997)). Expression of protein levels was assessed by preparing whole cell lysates and visualizing FLAG protein expression by immunoblotting as described below. Transfected pSMCs that were obtained from two transfections performed independently were used in subsequent experiments and results obtained were consistent between the two groups of cells.

Cell Lysis.

Cells were plated at a density of $5 \times 10^5$ in a 10 cm dishes (Falcon #3003) then grown to 90% confluency (approximately $5 \times 10^6$ cells). Cells were incubated overnight in serum free medium with 0.5% bovine serum albumin (SFM) and then pretreated with either the monoclonal anti IAP antibody (B6H12) or an irrelevant control monoclonal antibody for 2 hours (4 µg/ml) when required then treated with either 100 ng/ml IGF-1 or 10 ng/ml PDGF for the appropriate length of time prior to lysis in ice-cold lysis buffer: 50 mM Tris HCL (pH 7.5), 150 mM NaCl, 1% NP40, 0.25% sodium deoxycholate, 1 mM EGTA plus 1 mM sodium orthovanadate, 1 mM sodium fluoride, 1 mM PMSF, 1 µg/ml pepstatin A, 1 µg/ml leupeptin, 1 µg/ml aprotinin. The lysates were clarified by centrifugation at 14,000×g for 10 minutes.

Immunoprecipitation.

Cell lysates were incubated overnight at 4° C. with the appropriate antibody (IGF-1R, SHPS-1 or B6H12 using a 1:500 dilution). Immune complexes were then precipitated by adding protein A sepharose and incubating for a further 2 hours at 4° C. The samples were then centrifuged at 14,000×g for 10 minutes and the pellets washed 4 times with lysis buffer. The pellets were resuspended in 45 µl of reducing or non-reducing Laemmeli buffer, boiled for 5 minutes and the proteins separated by SDS-PAGE, 8% gel.

Assessment of p42/p44 MAP Kinase Activation.

pSMCS were plated at $1 \times 10^6$ cells/well in six well plates DMEM-H with 0.5 FBS and incubated at 37° C. for 48 hours. Plates were then rinsed and incubated for a further 2 hours in fresh DMEM-H with 0.5% FBS. Cells were then incubated in SFM with or without 4 µg/ml of B6H12 or irrelevant control monoclonal antibody for 2 hours prior to exposure to IGF-1 (100 ng/ml) for 20 minutes. Cells were then lysed with 200 µl of Laemelli buffer and the proteins in 40 µl of cell lysate were then separated by SDS-PAGE (8% gel). The activation of p42/44 MAPK was determined by immunoblotting with an antibody specific for the dual phosphorylated (threonine$^{202}$ and tyrosine$^{204}$) protein (at a dilution of 1:1000) as described below. To control for differences in protein levels an equal volume of cell lysate from each sample was loaded on an additional 8% gel. Following separation and transfer total p42/p44 protein levels were determined using a polyclonal p42/p44 MAPK antibody (at a dilution of 1:1000).

Western Immunoblotting.

Following SDS-PAGE the proteins were transferred to Immobilon P membranes. The membranes were blocked in 1% BSA in Tris-buffered saline with 0.1% Tween (TBST) for 2 hours at room temperature then incubated with one of six primary antibodies (IGF-1R, SHP-2, SHPS-1, PY99, B6H12 or FLAG, 1:500 dilution) overnight at 4° C. and washed three times in TBST. Binding of the peroxidase labeled secondary antibody was visualized using enhanced chemiluminescence following the manufacturer's instructions (Pierce, Rockford Ill., USA) and the immune complexes were detected by exposure to autoradiographic film or using the GeneGnome CCD imaging system (Syngene Cambridge, UK Ltd).

Chemiluminescent images obtained were scanned using a DuoScan T1200 (AGFA Brussels, Belgium) and band intensities of the scanned images were analyzed using NIH Image, version 1.61. The Student's t test was used to compare differences between treatments. The results that are shown are representative of at least three separate experiments.

Cell Wounding and Migration Assay.

Cells were plated in six-well plates and grown to confluency over seven days with one media change. Wounding was performed as previously described (J. Jones et al., *Proc Natl Acad Sci USA* 93, 2482-7 (1996)). Briefly, a razor blade was used to scrape an area of cells leaving a denuded area and a sharp visible wound line. Six, one mm areas along the wound edge were selected and recorded for each treatment. The wounded monolayers were then incubated with SFM (plus 0.2% FBS) with or without 100 ng/ml IGF-1 or PDGF (10 ng/ml). The cells were then fixed and stained (Diff Quick, Dade Behring, Inc., Newark, Del., USA) and the number of cells migrating into the wound area was counted. At least five of the previously selected 1 mM areas at the edge of the wound were counted for each data point.

Assessment of Cell Proliferation

Cells were plated at 5000 cells/cm$^2$ on 24 well plates in DMEM-H with 2% FBS and allowed to attach and spread for 24 hours before changing medium to DMEM-H plus 0.2% human platelet poor plasma. Following a further 24-hour incubation cells were pre-incubated in the presence or absence of B6H12 or an irrelevant control monoclonal antibody (4 µg/ml) for 2 hours prior to the addition of IGF-1 (100 ng/ml). Each treatment was set up in triplicate. Cells were then incubated for 48 hours and final cell number in each well determined. The Student's t test was used to compare differences between treatments. The results that are shown represent the mean (±SEM) from three separate experiments.

C. Results

IAP Associates with SHPS-1 in Stably Attached pSMCs Via its Extracellular Domain.

FIG. 1A shows that in stably attached quiescent SMCs there is detectable association between IAP and SHPS-1 as determined by co-immunoprecipitation experiments using both anti IAP and anti SHPS-1 antibodies for immunoprecipitation.

In order to investigate the role of IAP association with SHPS-1 in IGF-1R signaling we developed two experimental models in which we disrupted the association between IAP and SHPS-1. The first approach was to use an anti-IAP monoclonal antibody, B6H12 to interfere with the binding of the two proteins. FIG. 1B shows that following incubation of quiescent pSMCs with the anti IAP monoclonal antibody (B6H12) the interaction between IAP and SHPS-1 is reduced (a 75±7.5% reduction (mean±S.E.M n=3)). Preincubation with an irrelevant control monoclonal antibody has no effect on the association between the two proteins.

The binding between IAP and SHPS-1 specifically requires an intact disulfide bond in IAP between cysteine 33 in the extracellular domain and cysteine 261 within the putative transmembrane domain (R. Rebres et al., *J Biol Chem* 276, 7672-80 (2001)). If this bond is disrupted by mutagenesis the interaction of IAP with αVβ3 is preserved but binding to SHPS-1 is eliminated. We therefore generated and expressed two mutant forms of IAP in which the association between IAP and SHPS-1 would be predicted to be disrupted. FIG. 1C (top panel) shows the level of expression of three forms of IAP that were used in subsequent experiments. These included a) the FLAG tagged mutant form of IAP in which the complete extracellular domain has been deleted at amino acid residue 135 (IAPcyto), b) the FLAG tagged mutant form of IAP in which the two cysteine residues 33 and 261 had been substituted with serines (IAPc-s) and c) the FLAG tagged full length IAP (IAPfl).

A representative experiment shown in FIG. 1C (lower panels) shows that disruption of the extracellular domain of IAP alters its ability to associate with SHPS-1. Expression of IAP cyto results in a 88±6.4% (mean±SEM n=3) reduction in IAP association with SHPS-1 compared with association in cells expressing IAP fl. Since truncation of the extracellular domain of IAP also disrupts its association with αVβ3 we analyzed the SHPS-1/IAP interaction in cells expressing the IAPc-s mutation. In cells expressing IAP c-s there is an 81±4.5% (mean±SEM n=3) reduction in IAP association with SHPS-1 compared with cells expressing IAPfl. The control immunoblots show that similar levels of SHPS-1 were immunoprecipitated.

Blocking IAP-SHPS-1 Association Inhibits IGF-1 Stimulated SHPS-1 Phosphorylation and SHP-2 Recruitment.

Figure 2:
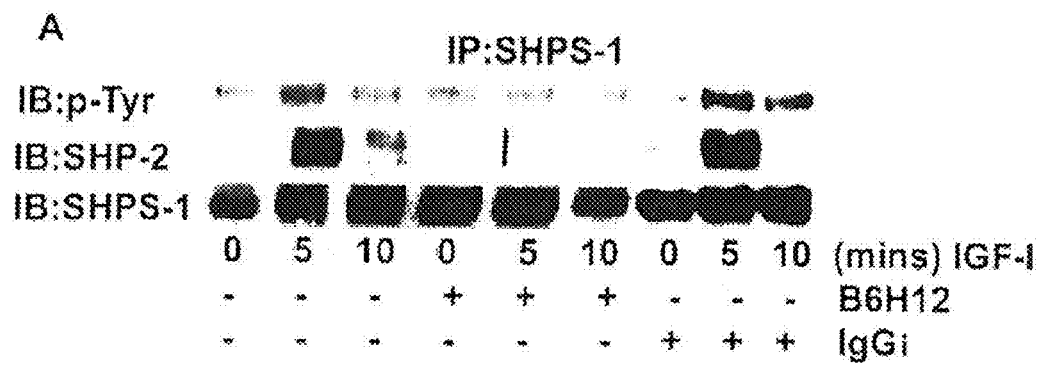
FIGS. 2A-C. A. SHPS-1 phosphorylation and SHP-2 recruitment to SHPS-1 in response to IGF-1 following disruption of the association between IAP and SHPS-1 by the anti IAP antibody, B6H12. Quiescent cells were incubated for two hours±B6H12 antibody or irrelevant control monoclonal antibody (both at 4 µg/ml) then exposed to IGF-1 (100 ng/ml) as indicated. Cell lysates were immunoprecipitated with an anti-SHPS-1 antibody then SHPS-1 phosphorylation was determined by immunoblotting with an antiphosphotyrosine antibody (p-Tyr). The association of SHP-2 with SHPS-1 was visualized by immunoblotting using an anti SHP-2 antibody. The amount of SHPS-1 protein in each lane is shown in the lower panel. The increase in SHPS-1 phosphorylation and SHP-2 recruitment following IGF-1 stimulation as determined by scanning densitometry analysis of western immunoblots from three separate experiments is shown. p<0.05 when cells preincubated with B6H12 are compared with cells preincubated in SFM alone. B SHPS-1 phosphorylation and SHP-2 recruitment in response to IGF-1 following disruption of the association between IAP and SHPS-1 in cells expressing mutated forms of IAP. Cells were exposed to IGF-1 (100 ng/ml) for various periods. Cell lysates were immunoprecipitated with an anti-SHPS-1 antibody and SHPS-1 phosphorylation was determined by immunoblotting with an antiphosphotyrosine antibody (pTyr). The association of SHP-2 was visualized by immunoblotting using an anti SHP-2 antibody. The amount of SHPS-1 protein in each lane is shown in the lower panel. The increase in SHPS-1 phosphorylation and SHP-2 recruitment following IGF-1 stimulation as determined by scanning densitometry analysis of western immunoblots from three separate experiments is shown. p<0.05 when cells expressing mutant forms of IAP are compared with cells expressing IAP fl. C. SHPS-1 phosphorylation in response to PDGF. Cells were exposed to PDGF (10 ng/ml) for 5 minutes. Following cell lysis and immunoprecipitation with an anti SHPS-1 antibody SHPS-1 phosphorylation was determined by immunoblotting with an anti phosphotyrosine antibody (pTyr).
Figure 2:
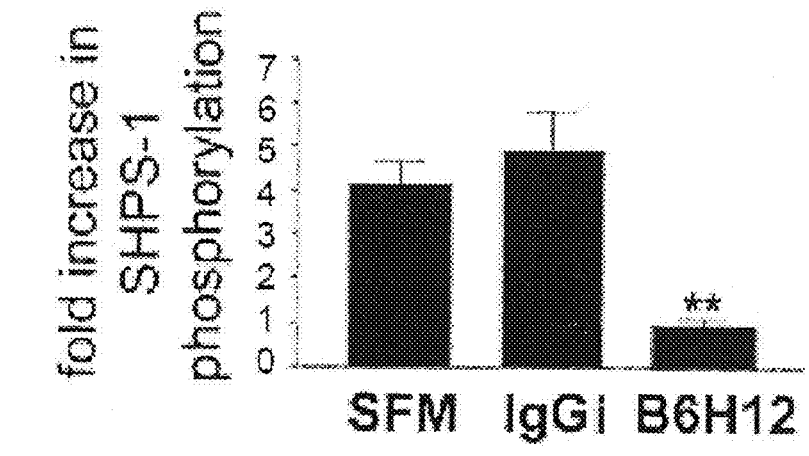
Figure 2:
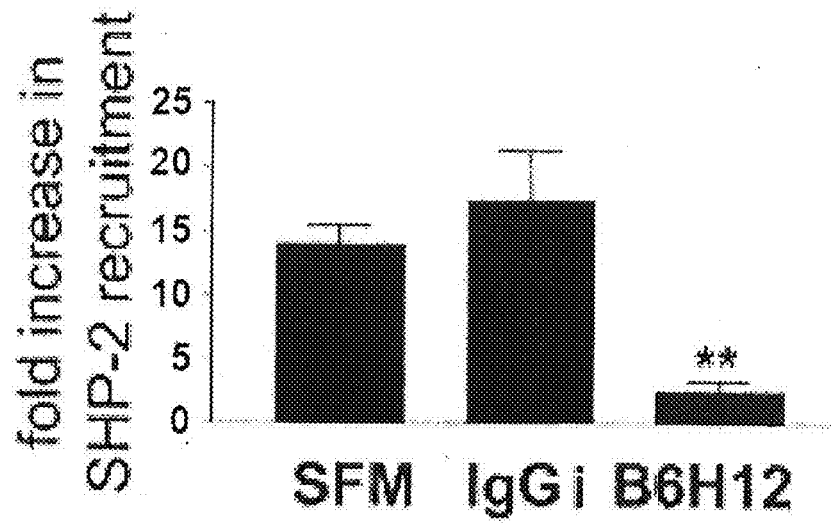
Figure 2:
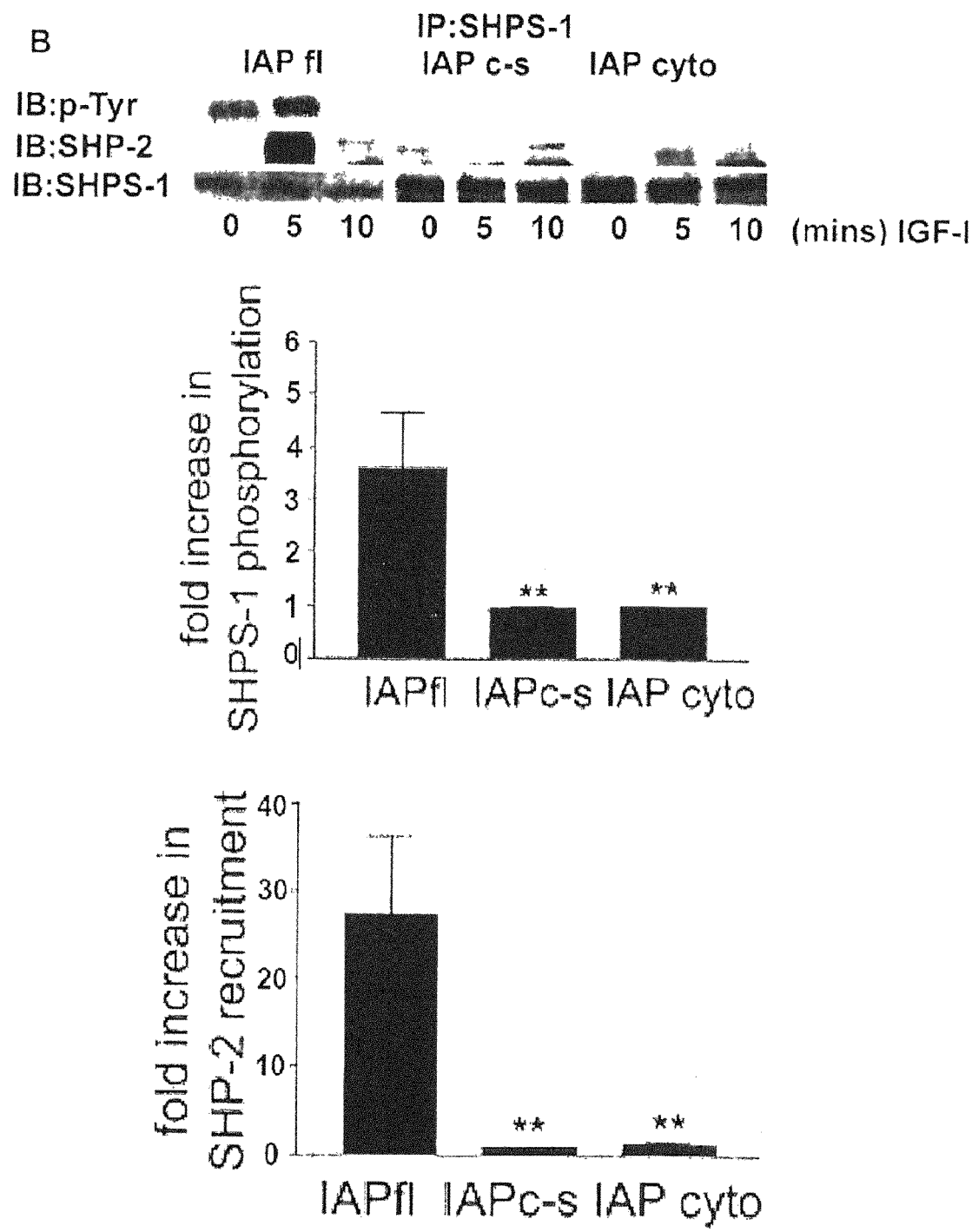
Figure 2:
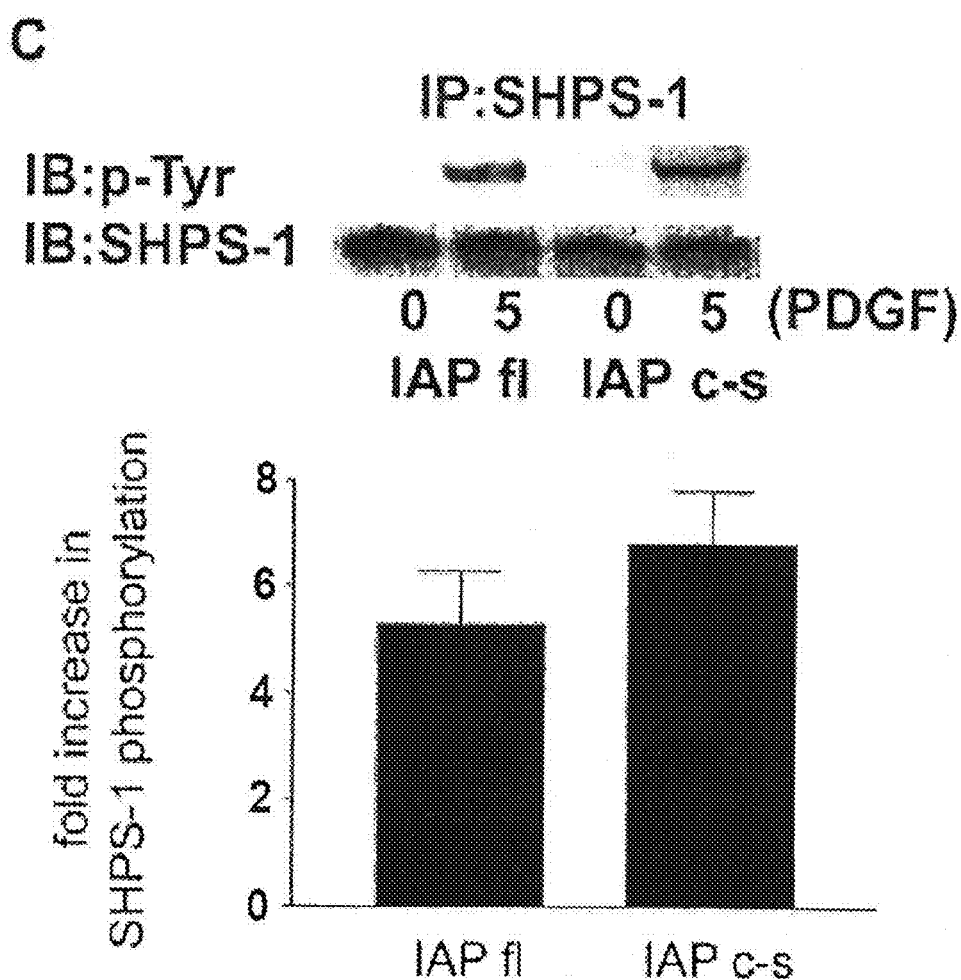

To determine the functional consequences of loss of physical association between IAP and SHPS-1 we examined SHPS-1 phosphorylation in response to IGF-1 in wild type cells pretreated with the anti IAP monoclonal antibody B6H12. A representative experiment is shown in FIG. 2A and it can be seen that in contrast to the 4.1±0.9 (mean±SEM n=3) fold increase in SHPS-1 phosphorylation in response to IGF-1 in controls, cells pretreated with B6H12 show a significant decrease (0.93±0.12 (mean±SEM n=3 p<0.05) in the IGF-1 stimulated increase in SHPS-1 phosphorylation. In cells preincubated with an irrelevant control monoclonal antibody IGF-1 stimulated SHPS-1 phosphorylation did not differ significantly from control cells. As can also been seen in FIG. 2A this reduction in SHPS-1 phosphorylation in the presence of B6H12 is associated with a significant decrease in IGF-1 stimulated recruitment of SHP-2 to SHPS-1 (a 1.8±1.1 fold increase in SHP-2 association in the presence of B6H12 compared with a 14±1.5 fold increase in control cells (mean±SEM n=3 p<0.05). Again there was no significant effect on IGF-1 stimulated recruitment of SHP-2 to SHPS-1 in cells preincubated with an irrelevant control monoclonal antibody.

The Extracellular Domain of IAP is Required for IGF-1 Stimulated SHPS-1 Phosphorylation and SHP-2 Recruitment.

In order to confirm the previous observation that suggested blocking IAP binding to SHPS-1 inhibited IGF-1 stimulated SHPS-1 phosphorylation the ability of IGF-1 to stimulate SHPS-1 phosphorylation in cells expressing the mutant forms of IAP were compared with cells expressing wild type IAP. The results from a representative experiment are shown in FIG. 2B and it can be seen that in contrast to the 3.6±0.8 (mean±SEM n=3) increase in SHPS-1 phosphorylation in response to IGF-1 in cells expressing IAPfl, in cells expressing the IAPcyto mutant or IAP c-s mutant no significant increase in SHPS-1 phosphorylation in response to IGF-1 can be detected.

Consistent with the results obtained using B6H12 the lack of SHPS-1 phosphorylation observed in the cells expressing the mutant forms of IAP is associated with an inhibition in SHP-2 recruitment to SHPS-1 in response to IGF-1 (FIG. 2B).

Since SHPS-1 has been shown to be phosphorylated in response to several growth factors, we wished to investigate the specificity of the requirement of IAP binding to SHPS-1. FIG. 2C shows that PDGF induces a marked increase in SHPS-1 phosphorylation following 5 minutes exposure in cells expressing IAPfl. However, in contrast to IGF-1, PDGF also stimulated SHPS-1 phosphorylation in the IAPc-s cells.

Figure 3:
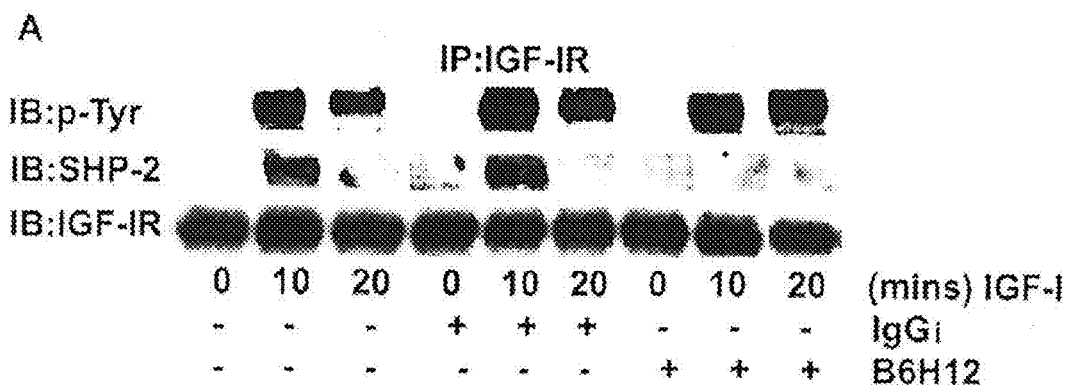
FIGS. 3A-B. IGF-1R phosphorylation time course and SHP-2 recruitment following disruption of the interaction between IAP and SHPS-1. A. Quiescent cells were incubated±B6H12 (4 µg/ml) then exposed to IGF-1 (100 ng/ml) for various lengths of time. Following lysis and immunoprecipitation with an anti IGF-1R antibody phosphorylation of the receptor was determined by immunoblotting with an anti phosphotyrosine antibody (pTyr). The association of SHP-2 was determined by immunoblotting with an anti SHP-2 antibody. The amount of IGF-1R protein in each lane is shown in the lower panel. The level of tyrosine phosphorylation of IGF-1R as a percentage of maximum phosphorylation detected as determined by scanning densitometry analysis of western immunoblots from three separate experiments is shown. The increase in SHP-2 recruitment following IGF-1 stimulation as determined by scanning densitometry analysis of western immunoblots from three separate experiments is also shown. p<0.05 when cells preincubated with B6H12 are compared with cells preincubated in SFM alone. B. Cells were incubated with IGF-1 (100 ng/ml) for various times. Following lysis and immunoprecipitation with an anti IGF-1R antibody phosphorylation of the receptor was determined by immunoblotting with an anti phosphotyrosine antibody (pTyr). The association of SHP-2 was determined by immunoblotting with an anti SHP-2 antibody. The amount of IGF-1R protein in each lane is shown in the lower panel. The changes IGF-1R phosphorylation and SHP-2 recruitment following IGF-1 stimulation as determined by scanning densitometry analysis of western immunoblots from three separate experiments is shown. $p<0.05$ when cells expressing IAPc-s are compared with cells expressing IAP fl.
Figure 3:
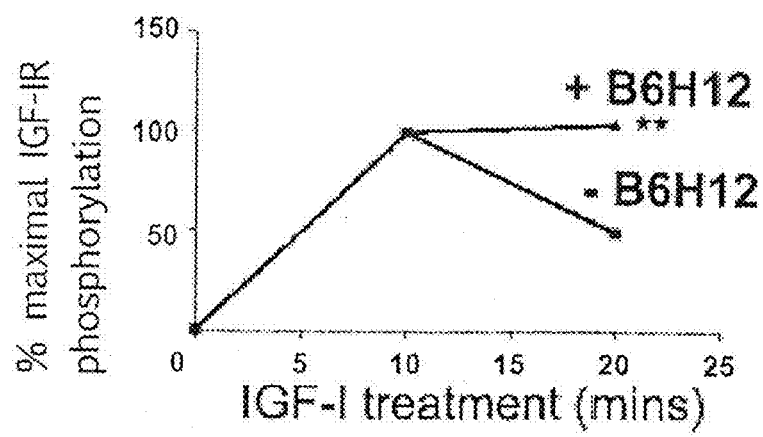
Figure 3:
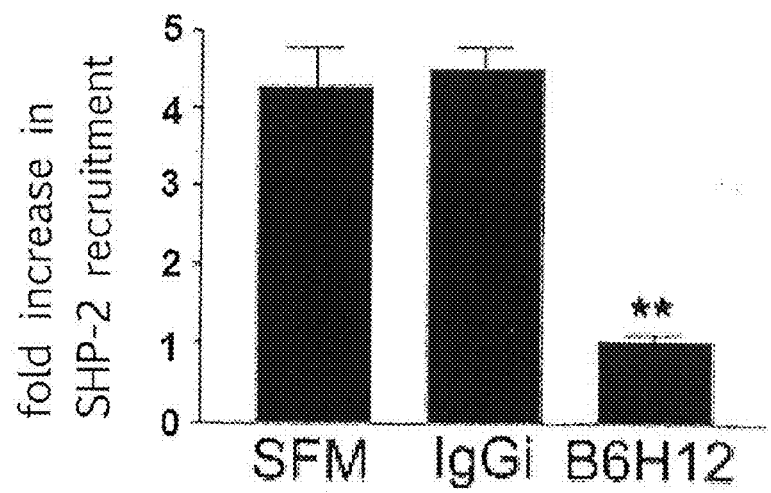
Figure 3:
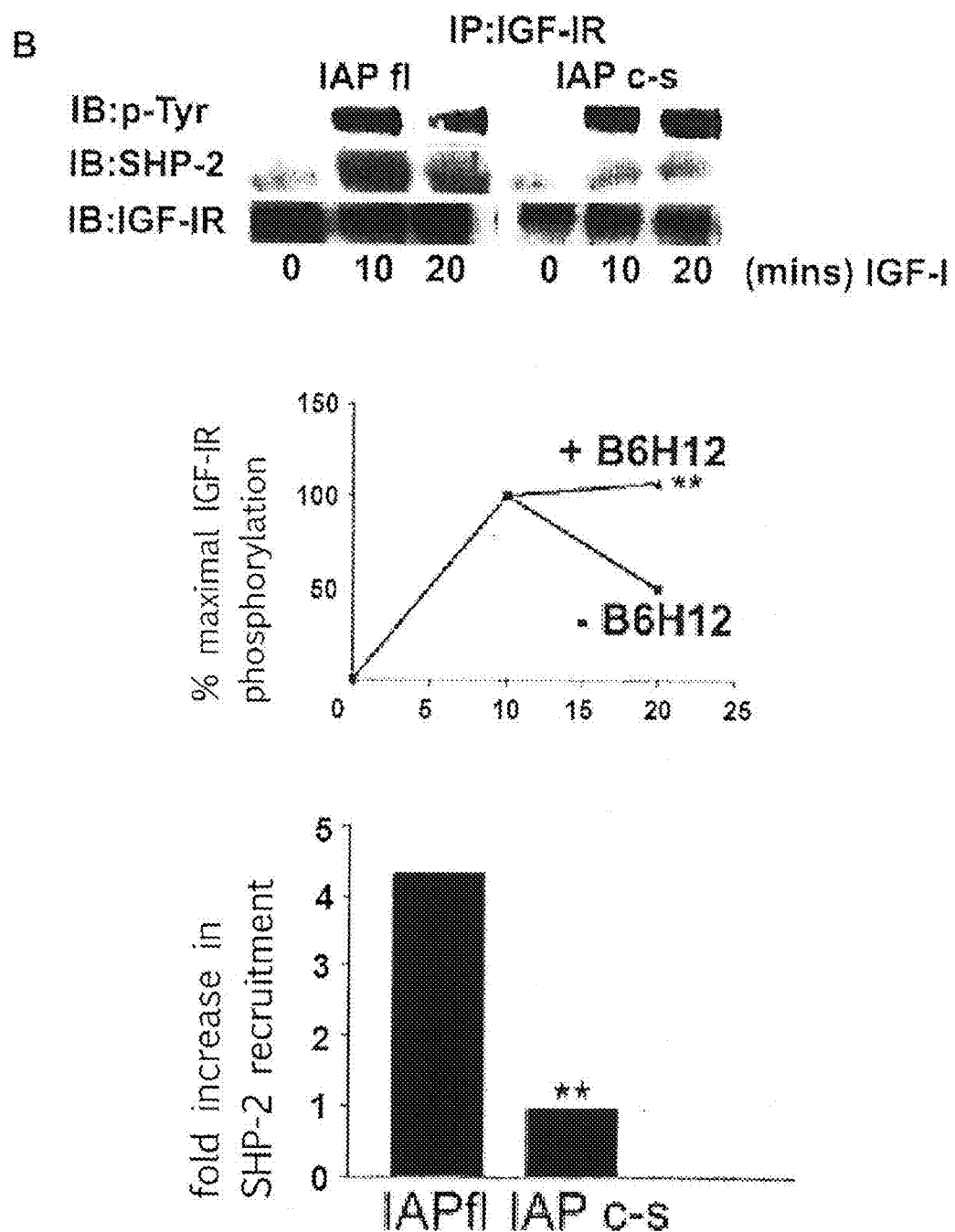

The association between the extracellular domain of IAP and SHPS-1 regulates the duration of IGF-1R phosphorylation via its modulation of SHP-2 recruitment. Phosphorylation of SHPS-1 is required for SHP-2 transfer to the IGF-1R and thereby regulates the duration of IGF-1R phosphorylation (T. Noguchi et al., *J Biol Chem* 271, 27652-8 (1996)), therefore we examined IGF-1R recruitment of SHP-2 and the duration of IGF-1R phosphorylation in cells pre treated with B6H12 and cells expressing the mutant forms of IAP. In control cells IGF-1 stimulates a 3.3±0.4 (mean±SEM n=3) fold increase in SHP-2 recruitment to the IGF-1 receptor following 10 minutes treatment with IGF-1. However in cells pretreated with B6H12 recruitment of SHP-2 to the IGF-1R there is no significant increase seen in SHP-2 recruitment to the IGF-1R. Consistent with our previous results (L. Maile and D. Clemmons, *J Biol Chem* 277, 8955-60 (2002)) the recruitment of SHP-2 to the IGF-1R precedes a reduction in receptor phosphorylation observed following 20 minutes IGF-1 stimulation. However, in cells preincubated with B6H12 consistent with the lack of SHP-2 recruitment no reduction in IGF-1R phosphorylation is detectable at the 20-minute time point. To confirm that the lack of SHP-2 recruitment to the IGF-1R in the cells pretreated with B6H12 was due to the specific disruption between IAP/SHPS-1 we examined IGF-1R phosphorylation in cells expressing IAPc-s. FIG. 3B shows that in these cells there is no increase in the recruitment of SHP-2 to the IGF-1R in response to IGF-1 and again this is associated with is a decrease in the amount of IGF-1R dephosphorylation observed following 20 minutes stimulation with IGF-1 in cells expressing full length IAP.

IGF-1 Stimulated MAPK Activity is Inhibited Following Disruption of SHP-2 Transfer.

Previous studies have shown that expression of an inactive form of SHP-2 results in an inhibition of IGF-1 stimulated MAPK (S. Manes et al., *Mol Cell Biol* 4, 3125-35 (1999)). To examine the consequence of the lack of SHP-2 transfer following the disruption of IAP-SHPS-1 binding we examined the activation of MAPK in response to IGF-1 in the presence of B6H12.

Figure 4A:
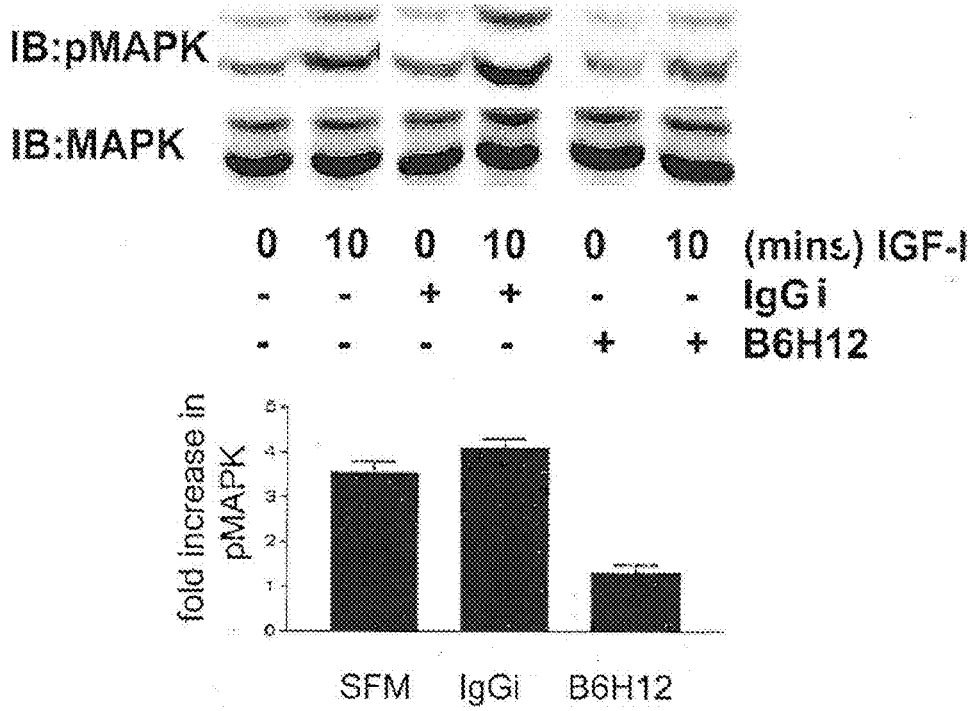
FIGS. 4A-B. A. Phosphorylation of MAPK in response to IGF-1. Cells were plated and grown prior to a 2-hour incubation±B6H12 or irrelevant control monoclonal antibody (both at 4 μg/ml) then treated with IGF-1 (100 ng/ml) for 10 minutes. The level of p42/44 MAPK phosphorylation was determined by immunoblotting with a phosphospecific MAPK antibody. The total amount of MAPK in each sample was determined by immunoblotting with a MAPK antibody. B. Cells were plated and grown prior to a 2 hour incubation±B6H12 or an irrelevant control monoclonal antibody (both at a concentration of 4 μg/ml) then treated with IGF-1 (100 ng/ml) for 48 hours. Cell number in each well was then determined. Each data point represents the mean of three independent experiments. **$p=<0.05$ when cell number in the cultures incubated in the presence of B6H12 are compared with cell number in the cultures incubated in the absence of antibody.

FIG. 4A shows that 10 minutes IGF-1 treatment stimulates a marked increase in the activation of MAPK as determined by the assessment of the dual phosphorylation of p42/p44 MAPK (70±5% S.E.M., n=4). However, when cells were preincubated with B6H12, IGF-1 was unable to stimulate a sustained increase in p42/p44 MAPK phosphorylation. MAPK is required for IGF-1 to stimulate cell proliferation.

Figure 4B:
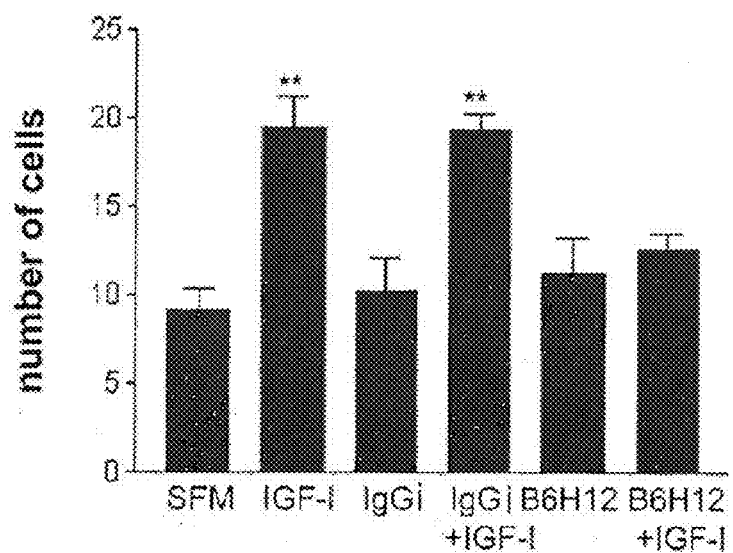

To examine the consequence of the disruption in IAP-SHPS-1 association on IGF-1 action in SMCs we determined the effect of B6H12 on IGF-1 stimulated cell proliferation. FIG. 4B shows that in IGF-1 stimulates a 2.2±0.2 (mean±SEM n=3) fold increase in cell proliferation. However when cells are incubated with B6H12 there is a significant reduction in IGF-1 stimulated cell proliferation (1.03±0.01 mean±SEM n=3 p<0.05 compared with cells incubated in the absence of B6H12. The inhibition in cell proliferation is consistent with the inhibition of IGF-1 stimulated MAPK activation.

Disruption of the IAP Interaction with SHPS-1 Inhibits IGF-1 Stimulated Cell Migration.

Figure 5:
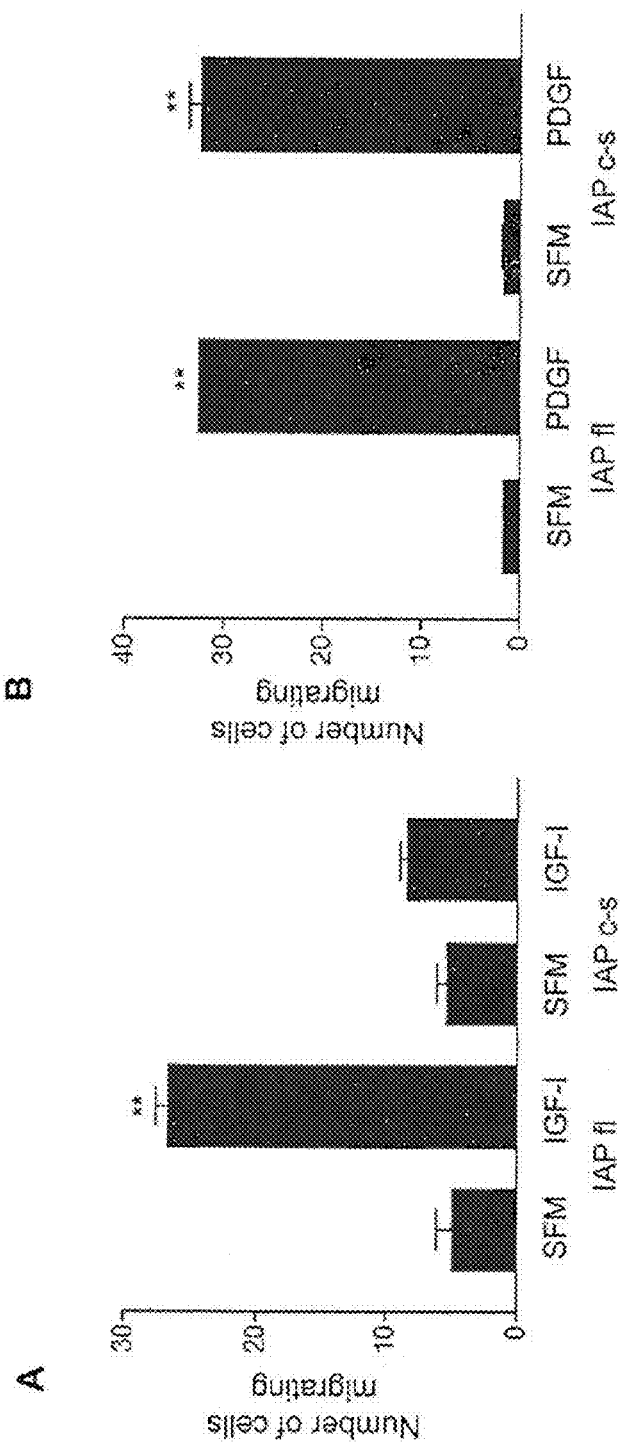
FIG. 5. IGF-1 stimulated cell migration in cells expressing full-length IAP and IAP C-S. Confluent cells were wounded then incubated±IGF-1 (100 ng/ml) for 48 hours. The number of cells migrating across the wound edge in at least 5 pre-selected regions were counted. Each data point represents the mean±S.E.M. of three independent experiments. **$p<0.05$ when migration in the presence of IGF-1 is compared with incubation in SFM alone.

We have previously reported that the preincubation of pSMCs with B6H12 inhibits IGF-1 stimulated migration in part by altering the interaction between IAP and αVβ3 (L. Maile et al., *J Biol Chem* 277, 1800-5 (2002)). To determine whether at least part of the effect B6H12 was also due to the inhibition of IAP binding to SHPS-1 we compared cell migration in response to IGF-1 in cells expressing IAP fl and the IAP c-s mutant. In FIG. 5 it can be seen that IGF-1 stimulated a significant increase in pSMC migration in cells expressing IAP fl. However, in cells expressing the IAP c-s mutant IGF-1 stimulated migration is significantly reduced. In contrast, PDGF stimulated cell migration of the IAP c-s cells is not significantly different to cells expressing full length IAP.

D. Discussion

The role of SHPS-1 in intracellular signaling has largely been attributed to the recruitment of SHP-2 to the phosphorylated tyrosines contained within ITIM motifs in the cytoplasmic tail of SHPS-1 and the subsequent activation of SHP-2 phosphatase activity (L. Maile et al., *J Biol Chem* 277, 1800-5 (2002); T. Takada et al., *J Biol Chem* 273, 9234-42 (1998); J. Timms et al., *Curr Biol* 9, 927-30 (1999)). The requirement for transfer of activated SHP-2 to downstream signaling molecules for growth factors such as IGF-1 to stimulate their physiologic actions has been strongly suggested by studies showing that expression of dominant negative forms of SHP-2 result in failure to properly activate growth factor stimulated increases in MAP kinase (T. Noguchi et al., *Mol Cell Biol* 14, 6674-82 (1994); K. Milarski and A. Saltiel, *J Biol Chem* 269, 21239-43 (1994); S. Xiao et al., *J Biol Chem* 269, 21244-8 (1994); K. Yamauchi et al., *Proc Natl Acad Sci USA* 92, 664-8 (1995); G. Pronk et al., *Mol Cell Biol* 14, 1575-81 (1994); T. Sasaoka et al., *J Biol Chem* 269, 10734-8 (1994)) and PI-3 kinase (C. Wu et al., *Oncogene* 20, 6018-25 (2001); S. Ugi et al., *J Biol Chem* 271, 12595-602 (1996); S. Zhang et al., *Mol Cell Biol* 22, 4062-72 (2002)) as well as failure to recruit SHP-2 to downstream signaling molecules. For IGF-1 it was specifically shown that expression of a dominant negative SHP-2 mutant resulted in a failure to activate MAP kinase or cell migration in response to IGF-1 (S. Manes et al., *Mol Cell Biol* 4, 3125-35 (1999)). The results from this study have demonstrated that the interaction between the IAP and SHPS-1 is a key regulator of IGF-1 signaling since our data has shown that the interaction is necessary for SHP-2 recruitment and transfer. Disruption of the interaction between the two proteins using two independent approaches resulted in a loss of SHP-2 recruitment to SHPS-1 and subsequent transfer to the IGF-1R which was reflected in prolonged IGF-1R phosphorylation. The consequence of lack of SHP-2 recruitment and transfer was evident in the inability of IGF-1 to stimulate MAPK activation and subsequently cell proliferation or cell migration.

The interaction between SHPS-1 and IAP was first suggested by experiments that demonstrated that anti IAP monoclonal antibodies blocked the attachment of cerebellar neurons, erythrocytes and thymocytes to a substratum containing P84 (a brain homolog of SHPS-1) (P. Jiang et al., *J Biol Chem* 274, 559-62 (1999); M. Seiffert et al., *Blood* 94, 3633-43 (1999)). That this interaction might play a role in cell-to-cell attachment was substantiated in experiments which demonstrated that the expression of the extracellular domain of SIRPα in SIRP negative cells supported adhesion of primary hematopoietic cells and this interaction was again inhibited by anti IAP monoclonal antibodies (E. Vernon-Wilson et al., *Eur J Immunol* 30, 2130-2137 (2000)).

Cell adhesion molecules mediating either cell attachment to the extracellular matrix, for example integrins and cell to cell adhesion molecules, for example cadherins, are important not only for cell attachment but also for the regulation of cell proliferation, survival and differentiation. The regulation of growth factor signaling by integrin receptors has been well documented. We have previously reported that ligand occupancy of αVβ3 is necessary for IGF-1 stimulated receptor signaling and a similar cooperative relationship between αVβ3 and the PDGF receptor has also been described (S. Miyamoto et al., *J. Cell. Biol.* 135: 16633-1642 (1996). IGF-1 has been shown to be a regulator of various homophilic cell to cell adhesion molecules. Guvakova et al reported that the IGF-1R colocalizes with E-cadherin and increases cell adhesion of MCF-7 cells by increasing expression of ZO-1 which binds to E-cadherin and stabilizes its interaction with the cytoskeleton (L. Mauro et al., *J. Biol. Chem.* 276: 3982-39897). Conversely, it has also been shown in human colonic tumor cells that IGF-1 via its ability to stimulate E-cadherin phosphorylation results in reduced membrane levels of E-cadherin and associated reduction in cell adhesion. IGF-1 has also been reported to downregulate T-cadherin expression again this was associated with a decrease in cell adhesion. Despite the apparent role of cell to cell adhesion receptors in regulating cell function there is little data regarding their ability to regulate growth factor action. It has been shown previously that the interaction of neuronal cell adhesion molecules with the fibroblast growth factor receptor leads receptor activation by autophosphorylation. VEGF has been shown to result in an increase in CEACAM expression and at least some of the effects of VEGF are mediated through CEACAM-1. The results from our experiments demonstrate that the interaction of the cell to cell adhesion molecules IAP and SHPS-1, in addition to mediating cell adhesion, also play an important regulatory role in growth factor signaling. Given the importance of cell to cell adhesion molecules in regulating cell function it is reasonable to conclude that the regulation of growth factor signaling by cell to cell adhesion molecules is a general mechanism for regulating growth factor action. Although PDGF signaling was not affected by disruption of the IAP-SHPS-1 interaction it will be interesting to determine whether other cell to cell adhesion molecules play a similar role in regulating PDGF and other growth factor signaling.

Since PDGF could still stimulate SHPS-1 phosphorylation in the absence of IAP binding to SHPS-1 this suggests that PDGF and IGF-1 may stimulate SHPS-1 phosphorylation via two different kinases. SHPS-1 has been shown to be phosphorylated directly by the insulin receptor kinase (Y. Fujioka et al., *Mol Cell Biol* 16, 6887-99 (1996)). Given the homology between the tyrosine kinase domains in the insulin and IGF-1R (e.g. 84%) it is possible that SHPS-1 is also a direct substrate for the IGF-1R kinase. IAP binding to SHPS-1 could modulate this process by localizing SHPS-1 in close proximity to the receptor kinase or alternatively IAP binding to SHPS-1 could alter the conformation of the SHPS-1 cytoplasmic domain making its tyrosines accessible to the IGF-1R kinase.

By virtue of its ability to stimulate SMC migration and proliferation IGF-1 is likely to be an important contributor to the development of atherosclerosis (J. Jones et al., *Proc Natl Acad Sci USA* 93, 2482-7 (1996); M. Khorsandi et al., *J. Clin. Invest.* 90, 1926-1931 (1992); B. Cerek et al. *Circ. Res.* 66, 1755-1760 (1990); P. Hayry et al., *FASEB J.* 9, 1336-1344 (1995)). In mice in which IGF-1 was over expressed in SMCs there was an increase in the rate of neointimal formation after carotid injury that appeared to have resulted from increased SMC proliferation and migration. The effect was apparent despite equivalent levels of serum IGF-1 in plasma compared with control animals suggesting a paracrine effect of locally produced IGF-1 (B. Zhu et al., *Endocrinology* 142, 3598-3666 (2001)). Given the apparent role of IGF-1 in the development of atherosclerosis and the effect of this interaction on IGF-1 signaling it is likely that this system may play a role in the development of atherosclerosis and disruption of the interaction may represent a novel therapeutic strategy to specifically inhibit IGF-1 action. Current approaches to target IGF-1 signaling have focused on blocking the activity of the receptor itself using antibodies or peptides. Disrupting cell to cell adhesion molecule interactions that specifically inhibit growth factor signaling offers a novel therapeutic strategy. This approach, that utilizes a different and distinct molecular mechanism, may work in synergy with other strategies.

EXAMPLE 2

Treatment of Diabetic Retinopathy with a Monoclonal Antibody that Disrupts IAP Binding to SHPS-1

In Vivo Measurement of Vascular Permeability

Rats were injected with Nembutal (80 mg/kg) (Southern Anesthesia). Once deep anesthesia had been achieved, warmed Evans blue (45 mg/kg) (Fisher Scientific) solution was injected via the tail vein. After 2 hrs a lethal dose of anesthetic (100 mg/kg) was administered. The chest cavity was opened and a needle inserted into the left ventricle. The right atrium was clipped and blood was centrifuged at 12,000×g for 5 min. The rats were perfused with 1% paraformaldehyde in citrate then the eyes were removed and placed in PBS. The retinas were removed, lyophilized, and then resuspended in formamide and incubated at 70° C. After 18 hrs the retina/formamide was centrifuged at 13,000×g for 10 min.

A standard curve was generated using serial dilutions of Evans Blue (30 mg/ul). The absorbance of the standard curve as well as each retina was measured using a Nanodrop spectrophotometer (Thermo-Scientific) using an excitation and emission wavelength of 620 and 740 nm, respectively. The amount of Evans Blue permeation from each retina was calculated using this formula:

$$\frac{\text{Evans Blue } (\mu g)/\text{retina dry weight } (g)}{\text{Time-averaged Evans Blue concentration } (\mu g)}$$
$$\text{plasma } (\mu l) \times \text{circulation (h)}$$

Diabetes Induction Protocol

Control (CON) rats received an injection of vehicle. Streptozotocin (STZ) was given by intraperitoneal injection (50 mg/kg; 100 ml). After 6 days rats with blood glucose >350 mg/dl were denoted as having diabetes. The STZ treated group was divided into two groups. At 20 days post-injection, the first group received an injection of control, mouse IgG (5.0 mg/kg), every 72 hours for 30 days. The second received an injection of rat anti IAP antibody (5.0 mg/kg) every 72 hours for 30 days. The rats were weighed daily and if weight loss was apparent they received insulin (4-8 units/kg).

Cell Lysis, Immunoprecipitation and Immunoblotting

Lysates were prepared from endothelial cell monolayers that had been exposed to various treatments. They were immunoprecipitated and immune complexes were separated by SDS-PAGE and transferred to Immobilon filters (Millipore) prior to immunoblotting to visualize proteins. Antibodies used for immunoblotting were anti-phosphotyrosine (PY99, Santa Cruz), anti-SHPS-1 (BD Biosources), anti-occludin (Invitrogen).

In Vitro Permeability Assay

Transwell inserts (24 well) were coated with collagen 10 $\mu g/cm^2$ (BD Biosciences) for 1 hr at 22° C. HUVECs were plated on the coated inserts at $5 \times 10^4$ cells/ml/insert in growth medium (15 mM glucose). After 24 hrs, 500 µl of growth medium was placed in the lower chambers. After 24 hrs, medium was changed to SFM-199 (15 mM glucose) containing IGF-1 (50 ng/ml) plus anti IAP (1 µg/ml). After 14 hrs, fluorescently labeled dextran was added (Sigma) (0.5 mg/ml). After 1 hr, medium was removed from the lower chamber and the amount of FITC-dextran was measured in a fluorescence detecting microplate reader (FluorImager 595 Molecular Dynamics) (using excitation and emission wave lengths of 294 and 521 nm, respectively).

In Vitro Tube Formation Assay

Human umbilical vein endothelial cells were grown to confluence and then changed to SFM-199 containing IGF-1 (50 ng/ml), B6H12 (1 µg/ml) for 14 hr. They were trypsinized and resuspended in SFM-199 (15 mM glucose) and then plated on 24 well plates coated with 500 µl of growth factor reduced matrigel (BD Sciences) ($1.5 \times 10^5$ cells/ml/well). After 4 hours the plates were photographed at 10× and the number of tubes/$cm^2$ area in 6 random areas of each well was determined. One tube is the area between two branch points (shown in FIG. 7C as the area between two "x" markers on the image).

Results

Figure 6:
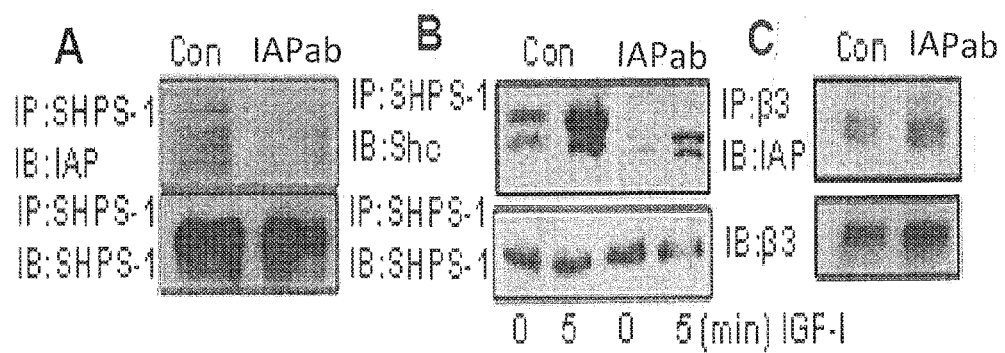
FIGS. 6A-C. Human endothelial cells were exposed to the anti-IAP antibody and lysates were immunoprecipitated with anti-SHPS-1 and then immunoblotted for IAP or Shc. A. The monoclonal antibody produced by the hybridoma having ATCC accession number PTA-13161 can disrupt IAP binding to SHPS-1. Cells were preincubated with the monoclonal antibody produced by the hybridoma having ATCC accession number PTA-13161 and then SHPS-1 was immunoprecipitated and the immunoprecipitate was immunoblotted for IAP. B. Sch, which has to bind to SHPS-1 to be activated in endothelial cells does not bind normally if the cells are pre-incubated with the monoclonal antibody produced by the hybridoma having ATCC accession number PTA-13161. C. The monoclonal antibody produced by the hybridoma having ATCC accession number PTA-13161 specifically disrupts IAP binding to SHPS-1 without disrupting IAP binding to $\beta_3$.

Two types of cells were used for the in vitro assays. The monoclonal antibody produced by the hybridoma having ATCC accession number PTA-13161, which is directed against amino acids 71 through 80 of the human IAP protein (amino acid numbering according to reference sequence provided herein) binds specifically to human IAP. FIG. 6A shows a comparison between control and this monoclonal antibody and provides a direct demonstration that this antibody can disrupt IAP binding to SHPS-1. The cells were pre-incubated with this monoclonal antibody, then SHPS-1 was immunoprecipitated and the immunoprecipitate was immunoblotted for IAP. Because the disruption results in inhibition of IGF-1 signaling one would expect critical signal transduction elements that are activated in response to IGF-1 to be inhibited. FIG. 6B shows that Sch, which has to bind to SHPS-1 to be activated in endothelial cells, does not bind normally if the cells are pre-incubated with this antibody. Most antibodies that react with IAP also bind to $\alpha_v\beta_3$. FIG. 6C shows that the monoclonal antibody produced by the hybridoma having ATCC accession number PTA-13161 is specific in that it disrupts IAP binding to SHPS-1 without disrupting IAP binding to $\beta_3$. This is important because disrupting IAP binding to $\beta_3$ could lead to side effects such as increased platelet aggregation. This is an important distinguishing feature of this antibody.

Figure 7:
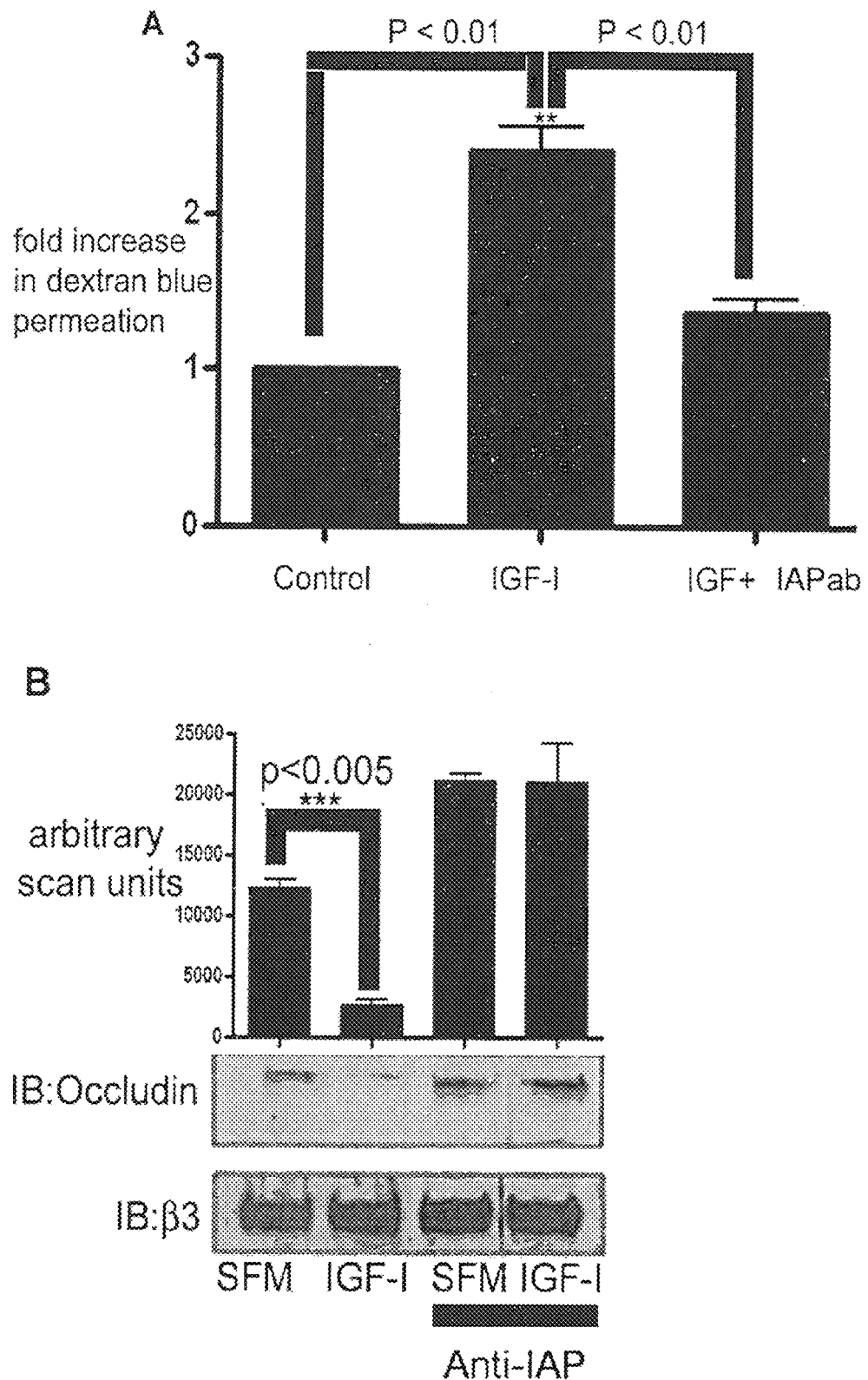
FIGS. 7 A-C. In vitro assay of capillary formation. A. Cell permeability measured in vitro based on dextran blue permeation. IGF-1 stimulates permeation and this is inhibited in the presence of the monoclonal antibody produced by the hybridoma having ATCC accession number PTA-13161. B. The tight junction protein occludin, which allows endothelial cells to form a permeability barrier, is disrupted in the presence of IGF-1, resulting in occludin leaving the junctional complex that is normally formed and diffusing out into the cell. In the presence of the monoclonal antibody produced by the hybridoma having ATCC accession number PTA-13161, this effect of IGF-1 is completely inhibited. C. Photomicrographs of endothelial cell tube formation. In IGF-1 treated cells, tube formation can be seen (upper right panel), where the capillary cells are joining each other with capillary tubes. In the presence of the monoclonal antibody produced by the hybridoma having ATCC accession number PTA-13161, this is completely disrupted, as shown in the lower two panels and on the bar graph, where the number of tubes per cm$^2$ is shown.
Figure 7:
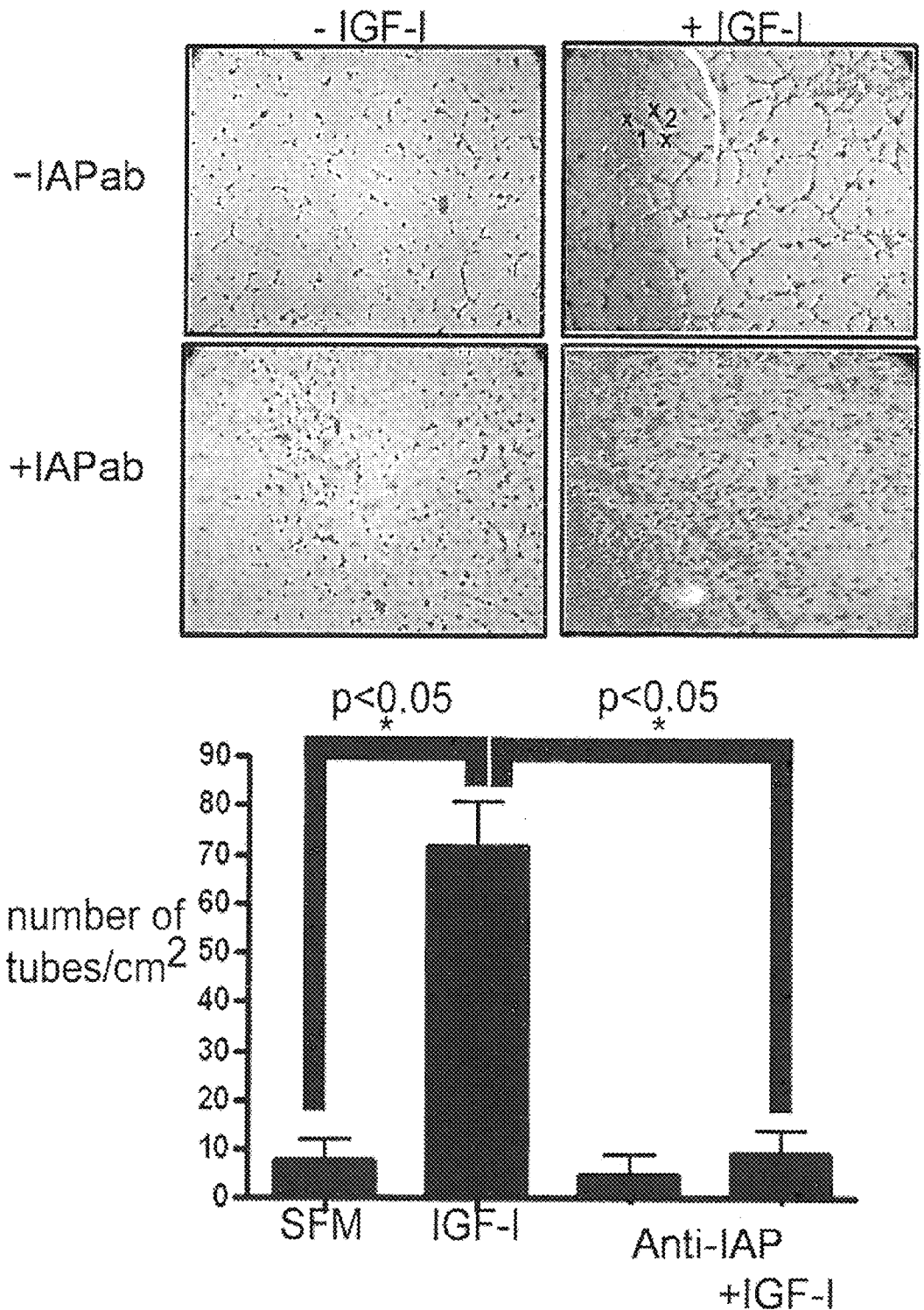

As a companion to this study, an experiment is shown wherein the ability of human endothelial cells to form tubes in an in vitro assay of capillary formation that occurs in vivo is demonstrated. Endothelial cell tube formation is shown in FIG. 7C. FIG. 7A shows cell permeability that is measured in vitro based on dextran blue permeation. The endothelial cells grow in monolayer much as they do in blood vessels and the ability of this dye to penetrate the monolayer is measured. As can be seen from FIG. 7A, IGF-1 stimulates permeation and this is inhibited in the presence of the IAP antibody. FIG. 7B shows that the tight junction protein occludin, which allows endothelial cells to form a permeability barrier, is disrupted in the presence of IGF-1; i.e., occludin leaves the junctional complex which is normally formed and diffuses out into the cell. That is why there is a decrease in immunoblot intensity of the occludin band. In the presence of the antibody produced by the hybridoma having ATCC accession number PTA-13161, this effect of IGF-1 is completely inhibited. In FIG. 7C, in IGF-1 treated cells tube formation can be seen, wherein the capillary cells are joining each other with capillary tubes. In the presence of the antibody produced by the hybridoma having ATCC accession number PTA-13161, this is completely disrupted as shown in the lower two panels of FIG. 7C and on the bar graph, where the number of tubes per cm$^2$ is shown.

Figure 8:
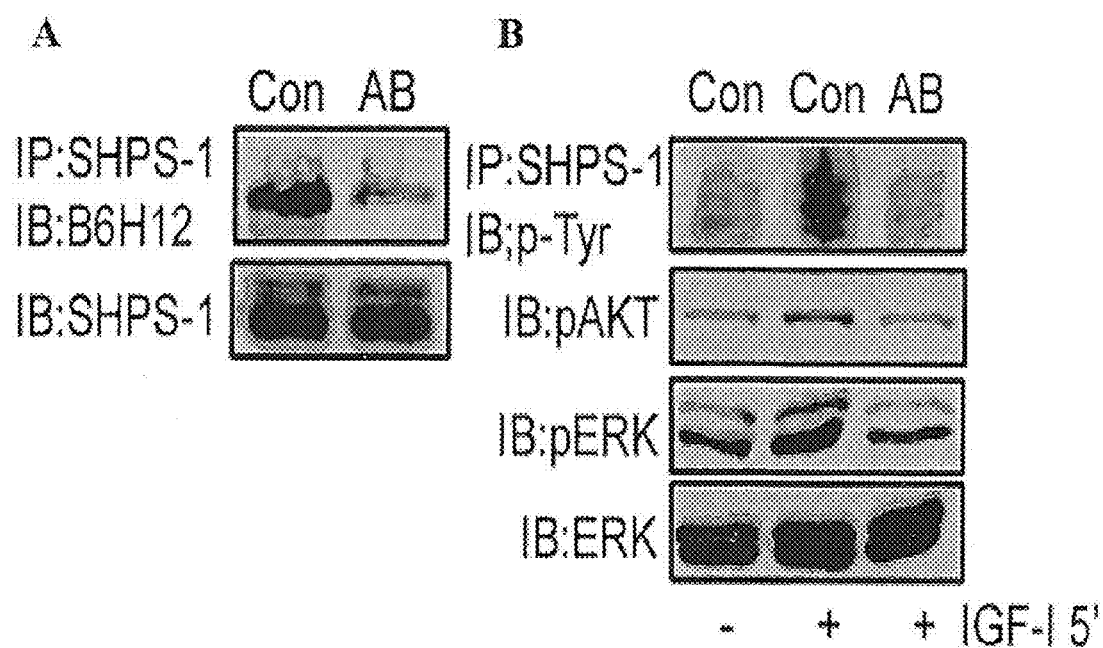
FIGS. 8A-B. Rat endothelial cells were cultured in 25 mM glucose. Following overnight in SFM, cells were incubated with rat anti-IAP antibody [that had been prepared using the rat IAP sequence NNKSTTREQN (amino acids 72-180 of the rat IAP sequence)] linked to KLH as an immunogen according to known methods (AB) or with a control antibody (Con). A. Control antibody had no effect on IAP/SHPS-1 association, wherein the anti-rat IAP antibody completely disrupted this association. B. Following IGF-1 stimulation, there is tyrosine phosphorylation of SHPS-1, stimulation of AKT and MAPK activation. These are inhibited in the presence of the anti-rat IAP antibody.
Figure 9:
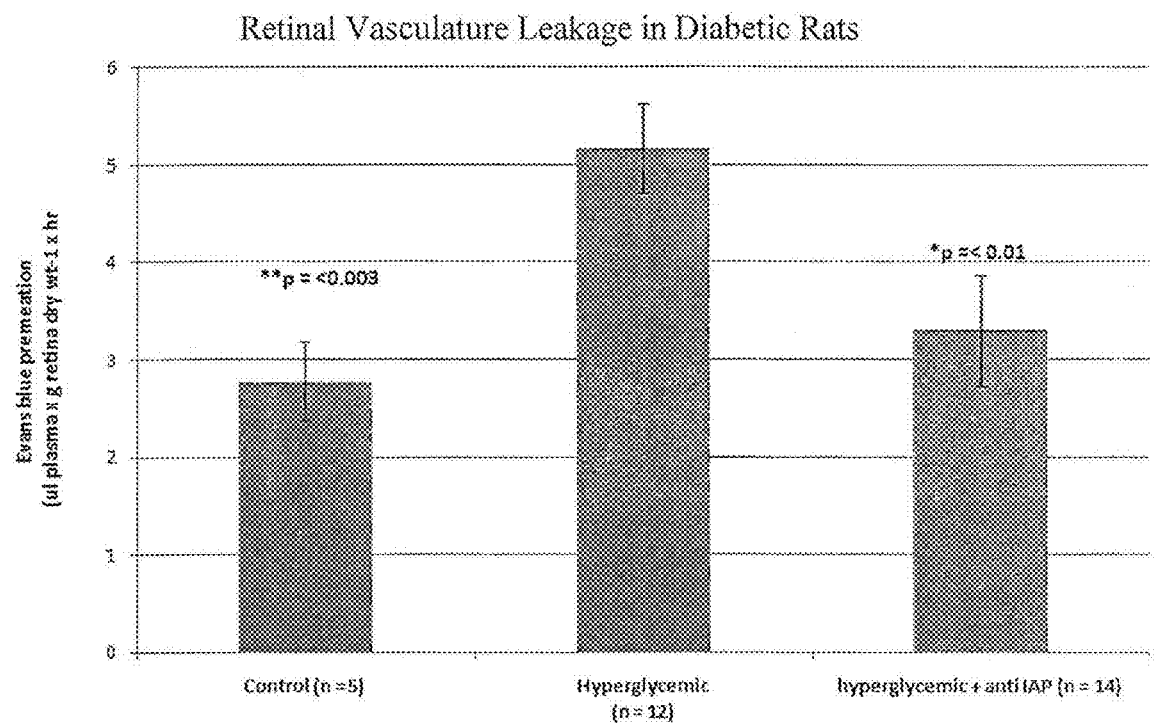
FIG. 9. Vascular permeability. Non diabetic rats are shown as Control (N=5). The diabetic rats were treated with control IgG (N=12) or IgG purified from antiserum that contained an anti-rat IAP antibody (N=14) by protein A sepharose chromatography. After three weeks the animals were anesthetized and then vascular permeability was measured. The anti-rat IAP IgG significantly inhibited retinal vein vascular permeability, which is one of the first changes that occur in diabetic retinopathy.

Studies described in FIGS. 8 and 9 were conducted in rat endothelial cells. This is because the amino acid sequence 71 through 80 of the IAP protein is not conserved across species. Because the amino acids are different in rat IAP as opposed to human IAP, studies were conducted to show that this amino acid sequence had the same functional significance. This was necessary because if the human antibody to IAP is administered to rats in vivo it would not work because this amino acid sequence is not conserved across species; therefore the human antibody would not be expected to disrupt rat IAP binding to rat SHPS-1. Therefore an anti-rat IAP antibody was prepared by immunizing rabbits with an immunogen that was comprised of a 10 amino acid sequence from rat IAP that was homologous to the human IAP sequence that was used to prepare the monoclonal antibody. As stated herein, this peptide was conjugated to KLH and rabbits were immunized. The IgG was then purified from rabbit serum using Protein A sepharose. This was the purified IgG that was injected into the rats to inhibit capillary permeability. This rat antibody was validated in the same way the human antibody was validated, to show that the rat antibody would inhibit IAP/SHPS-1 association in rat endothelial cells and that it would inhibit IGF-1 signaling. As shown in FIG. 8A, the control antibody (Con) had no effect on IAP/SHPS-1 interaction whereas the anti-rat IAP antibody (AB) completely disrupted their association. FIG. 8B shows that following IGF-1 stimulation, there is tyrosine phosphorylation of SHPS-1, stimulation of AKT and MAPK activation and that these are inhibited in the presence of the rat anti-IAP antibody.

FIG. 9 shows the results of an in vivo experiment in which the same antibody that disrupted SHPS1/IAP association in rats was injected into rats in vivo. This experiment was conducted over a three week period. The rats were made diabetic as described herein and then received injections of the purified anti-rat antibody twice a week. Evans blue dye permeation out of the retinal capillaries into the retina of the diabetic rats was then measured. As shown in FIG. 9, there is a major increase in capillary permeability in diabetic rats (hyperglycemic), which is a hallmark of diabetic retinopathy. As also shown in FIG. 9, injection of the rat anti-IAP antibody inhibited this increase in permeability. Vascular permeability is one of the first changes that occur in human diabetic retinopathy. This rat model demonstrates Evans blue leakage, which is a standard assay for measuring vascular permeability (see Kern "In vivo models of diabetic retinopathy" Contemporary Diabetes 2:137-151 (2008; Bhatt and Addepalli "Attenuation of diabetic retinopathy by enhanced inhibition of MMP-2 and MMP-9 using aspirin and minocycline in streptozotocin-diabetic rats" *Am. J. Transl. Res* 2(2):181-189 (2010)). Therefore it is known in the art as a surrogate animal model of these early changes that occur in human diabetic retinopathy. This leakage of vessels is directly linked to visual loss since it can result in fluid accumulation around the macula and macular damage is a known cause of severe visual loss in patients with diabetic retinopathy. Furthermore factors such as vascular endothelial growth factor inhibitors that inhibit this capillary leak have been shown to inhibit other changes that occur in diabetic retinopathy. In summary since the antibody directed against amino acids 71 through 80 of rat IAP (a region that is homologous to the same sequence in human IAP) inhibits retinal capillary leak it is expected that it will be an effective treatment for human diabetic retinopathy.

The foregoing is illustrative of the present invention, and is not to be construed as limiting thereof. The invention is defined by the following claims, with equivalents of the claims to be included therein.

The invention claimed is:

1. A monoclonal antibody that specifically binds an epitope within amino acids 71-80 of the human integrin associated protein (IAP) and is an antagonist of IAP to Src homology 2 (SH2) domain-containing protein tyrosine phosphatase substrate 1 (SHPS-1) binding.

2. The antibody of claim 1, coupled to a detectable group.

3. The antibody of claim 1, coupled to a therapeutic group.

4. The antibody of claim 1, wherein the antibody is a humanized antibody.

5. The antibody of claim 1, wherein the antibody does not disrupt IAP binding to a 63 protein.

6. A pharmaceutical formulation comprising the antibody of claim 1 in a pharmaceutically acceptable carrier.

7. The antibody of claim 1, wherein the antibody is selected from the group consisting of (a) the monoclonal antibody produced by the hybridoma cell line having ATCC accession number PTA-13161, and (b) a monoclonal antibody that competes for binding to the same epitope as the epitope bound by a monoclonal antibody produced by the hybridoma cell line having ATCC accession number PTA-13161.

8. The antibody of claim 7, coupled to a detectable group.

9. The antibody of claim 7, coupled to a therapeutic group.

10. The antibody of claim 7, wherein the antibody is a humanized antibody.

11. A pharmaceutical formulation comprising the antibody of claim 7 in a pharmaceutically acceptable carrier.

12. A monoclonal antibody produced by the hybridoma cell line having ATCC accession number PTA-13161.

13. The antibody of claim 12, coupled to a detectable group.

14. The antibody of claim 12, coupled to a therapeutic group.

15. The antibody of claim 12, wherein the antibody is a humanized antibody.

16. A pharmaceutical formulation comprising the antibody of claim 12 in a pharmaceutically acceptable carrier.

17. An antibody selected from the group consisting of (a) the monoclonal antibody produced by the hybridoma cell line having ATCC accession number PTA-13161, and (b) a monoclonal antibody that competes for binding to IAP with a monoclonal antibody produced by the hybridoma cell line having ATCC accession number PTA-13161.

* * * * *

UNITED STATES PATENT AND TRADEMARK OFFICE
CERTIFICATE OF CORRECTION

PATENT NO. : 9,475,882 B2
APPLICATION NO. : 14/076130
DATED : October 25, 2016
INVENTOR(S) : David R. Clemmons and Laura A. Maile It is certified that error appears in the above-identified patent and that said Letters Patent is hereby corrected as shown below:

In the Claims

Claim 5 reads: "The antibody of claim 1, wherein the antibody does not disrupt IAP binding to a 63 protein."

Should Read:

"The antibody of claim 1, wherein the antibody does not disrupt IAP binding to a β3 protein."

Signed and Sealed this
Third Day of January, 2017

Michelle K. Lee
*Director of the United States Patent and Trademark Office*

SEQUENCE LISTING

```
<160> NUMBER OF SEQ ID NOS: 17

<210> SEQ ID NO 1
<211> LENGTH: 17
<212> TYPE: DNA
<213> ORGANISM: Sus scrofa domesticus
<220> FEATURE:
<221> NAME/KEY: misc_feature
<222> LOCATION: (1)..(17)
<223> OTHER INFORMATION: RT-PCR primer
<220> FEATURE:
<221> NAME/KEY: misc_feature
<222> LOCATION: (1)..(17)
<223> OTHER INFORMATION: Nucleotides 121-139 of porcine IAP cDNA
       sequence
```

```
<400> SEQUENCE: 1
atgtggccct ggtggtc                                                    17

<210> SEQ ID NO 2
<211> LENGTH: 40
<212> TYPE: DNA
<213> ORGANISM: Artificial
<220> FEATURE:
<223> OTHER INFORMATION: RT-PCR primer
<220> FEATURE:
<221> NAME/KEY: misc_feature
<222> LOCATION: (1)..(3)
<223> OTHER INFORMATION: Completment encodes stop codon
<220> FEATURE:
<221> NAME/KEY: misc_feature
<222> LOCATION: (4)..(27)
<223> OTHER INFORMATION: Completment encodes FLAG sequence
<220> FEATURE:
<221> NAME/KEY: misc_feature
<222> LOCATION: (28)..(40)
<223> OTHER INFORMATION: Complementary to nucleotides 1005-1030 of
      porcine IAP cDNA sequence

<400> SEQUENCE: 2
tcatttgtcg tcgtcgtctt tgtagtcggt tgtatagtct                           40

<210> SEQ ID NO 3
<211> LENGTH: 29
<212> TYPE: DNA
<213> ORGANISM: Sus scrofa domesticus
<220> FEATURE:
<221> NAME/KEY: misc_feature
<222> LOCATION: (1)..(29)
<223> OTHER INFORMATION: Nucleotides 527-556 of porcine IAP cDNA
      sequence

<400> SEQUENCE: 3
tctccaaatg aaaaatcctc attgttatt                                       29

<210> SEQ ID NO 4
<211> LENGTH: 31
<212> TYPE: DNA
<213> ORGANISM: Artificial
<220> FEATURE:
<223> OTHER INFORMATION: Mutagenesis primer
<220> FEATURE:
<221> NAME/KEY: misc_feature
<222> LOCATION: (1)..(31)
<223> OTHER INFORMATION: Complementary to nucleotides 204-225 of the
      porcine IAP cDNA sequence with c to g substitution at position 16.

<400> SEQUENCE: 4
gtaacagttg tattggaaac ggtgaattct a                                    31

<210> SEQ ID NO 5
<211> LENGTH: 30
<212> TYPE: DNA
<213> ORGANISM: Artificial
<220> FEATURE:
<223> OTHER INFORMATION: Mutagenesis primer
<220> FEATURE:
<221> NAME/KEY: misc_feature
<222> LOCATION: (1)..(30)
<223> OTHER INFORMATION: Complementary to nucleotides 888-918 of the
      porcine IAP cDNA sequence with c to g substitution at position 16.

<400> SEQUENCE: 5
ccatgcactg gggtagactc tgagacgcag                                      30
```

```
<210> SEQ ID NO 6
<211> LENGTH: 305
<212> TYPE: PRT
<213> ORGANISM: Homo sapiens

<400> SEQUENCE: 6

Met Trp Pro Leu Val Ala Ala Leu Leu Leu Gly Ser Ala Cys Cys Gly
1               5                   10                  15

Ser Ala Gln Leu Leu Phe Asn Lys Thr Lys Ser Val Glu Phe Thr Phe
            20                  25                  30

Cys Asn Asp Thr Val Val Ile Pro Cys Phe Val Thr Asn Met Glu Ala
        35                  40                  45

Gln Asn Thr Thr Glu Val Tyr Val Lys Trp Lys Phe Lys Gly Arg Asp
    50                  55                  60

Ile Tyr Thr Phe Asp Gly Ala Leu Asn Lys Ser Thr Val Pro Thr Asp
65                  70                  75                  80

Phe Ser Ser Ala Lys Ile Glu Val Ser Gln Leu Leu Lys Gly Asp Ala
                85                  90                  95

Ser Leu Lys Met Asp Lys Ser Asp Ala Val Ser His Thr Gly Asn Tyr
            100                 105                 110

Thr Cys Glu Val Thr Glu Leu Thr Arg Glu Gly Glu Thr Ile Ile Glu
        115                 120                 125

Leu Lys Tyr Arg Val Val Ser Trp Phe Ser Pro Asn Glu Asn Ile Leu
    130                 135                 140

Ile Val Ile Phe Pro Ile Phe Ala Ile Leu Leu Phe Trp Gly Gln Phe
145                 150                 155                 160

Gly Ile Lys Thr Leu Lys Tyr Arg Ser Gly Gly Met Asp Glu Lys Thr
                165                 170                 175

Ile Ala Leu Leu Val Ala Gly Leu Val Ile Thr Val Ile Val Ile Val
            180                 185                 190

Gly Ala Ile Leu Phe Val Pro Gly Glu Tyr Ser Leu Lys Asn Ala Thr
        195                 200                 205

Gly Leu Gly Leu Ile Val Thr Ser Thr Gly Ile Leu Ile Leu Leu His
    210                 215                 220

Tyr Tyr Val Phe Ser Thr Ala Ile Gly Leu Thr Ser Phe Val Ile Ala
225                 230                 235                 240

Ile Leu Val Ile Gln Val Ile Ala Tyr Ile Leu Ala Val Val Gly Leu
                245                 250                 255

Ser Leu Cys Ile Ala Ala Cys Ile Pro Met His Gly Pro Leu Leu Ile
            260                 265                 270

Ser Gly Leu Ser Ile Leu Ala Leu Ala Gln Leu Leu Gly Leu Val Tyr
        275                 280                 285

Met Lys Phe Val Ala Ser Asn Gln Lys Thr Ile Gln Pro Pro Arg Asn
    290                 295                 300

Asn
305

<210> SEQ ID NO 7
<211> LENGTH: 17
<212> TYPE: PRT
<213> ORGANISM: Homo sapiens

<400> SEQUENCE: 7

Phe Val Thr Asn Met Glu Ala Gln Asn Thr Thr Glu Val Tyr Lys Trp
1               5                   10                  15

Lys
```

-continued

<210> SEQ ID NO 8
<211> LENGTH: 18
<212> TYPE: PRT
<213> ORGANISM: Homo sapiens

<400> SEQUENCE: 8

Lys Trp Lys Phe Lys Gly Arg Asp Ile Tyr Thr Phe Asp Gly Ala Leu
1               5                   10                  15

Asn Lys

<210> SEQ ID NO 9
<211> LENGTH: 21
<212> TYPE: PRT
<213> ORGANISM: Homo sapiens

<400> SEQUENCE: 9

Ser Thr Val Pro Thr Asp Phe Ser Ser Ala Lys Ile Glu Val Ser Gln
1               5                   10                  15

Leu Leu Lys Gly Asp
            20

<210> SEQ ID NO 10
<211> LENGTH: 17
<212> TYPE: PRT
<213> ORGANISM: Homo sapiens

<400> SEQUENCE: 10

Tyr Thr Phe Asp Gly Ala Leu Asn Lys Ser Thr Val Pro Thr Asp Phe
1               5                   10                  15

Ser

<210> SEQ ID NO 11
<211> LENGTH: 503
<212> TYPE: PRT
<213> ORGANISM: Homo sapiens

<400> SEQUENCE: 11

Met Glu Pro Ala Gly Pro Ala Pro Gly Arg Leu Gly Pro Leu Leu Cys
1               5                   10                  15

Leu Leu Leu Ala Ala Ser Cys Ala Trp Ser Gly Val Ala Gly Glu Glu
                20                  25                  30

Glu Leu Gln Val Ile Gln Pro Asp Lys Ser Val Ser Val Ala Ala Gly
            35                  40                  45

Glu Ser Ala Ile Leu His Cys Thr Val Thr Ser Leu Ile Pro Val Gly
        50                  55                  60

Pro Ile Gln Trp Phe Arg Gly Ala Gly Pro Ala Arg Glu Leu Ile Tyr
65                  70                  75                  80

Asn Gln Lys Glu Gly His Phe Pro Arg Val Thr Thr Val Ser Glu Ser
                85                  90                  95

Thr Lys Arg Glu Asn Met Asp Phe Ser Ile Ser Ile Ser Asn Ile Thr
            100                 105                 110

Pro Ala Asp Ala Gly Thr Tyr Tyr Cys Val Lys Phe Arg Lys Gly Ser
        115                 120                 125

Pro Asp Thr Glu Phe Lys Ser Gly Ala Gly Thr Glu Leu Ser Val Arg
    130                 135                 140

Ala Lys Pro Ser Ala Pro Val Val Ser Gly Pro Ala Ala Arg Ala Thr
145                 150                 155                 160

Pro Gln His Thr Val Ser Phe Thr Cys Glu Ser His Gly Phe Ser Pro
                165                 170                 175

Arg Asp Ile Thr Leu Lys Trp Phe Lys Asn Gly Asn Glu Leu Ser Asp
            180                 185                 190

Phe Gln Thr Asn Val Asp Pro Val Gly Glu Ser Val Ser Tyr Ser Ile
            195                 200                 205

His Ser Thr Ala Lys Val Val Leu Thr Arg Glu Asp Val His Ser Gln
            210                 215                 220

Val Ile Cys Glu Val Ala His Val Thr Leu Gln Gly Asp Pro Leu Arg
225                 230                 235                 240

Gly Thr Ala Asn Leu Ser Glu Thr Ile Arg Val Pro Pro Thr Leu Glu
            245                 250                 255

Val Thr Gln Gln Pro Val Arg Ala Glu Asn Gln Val Asn Val Thr Cys
            260                 265                 270

Gln Val Arg Lys Phe Tyr Pro Gln Arg Leu Gln Leu Thr Trp Leu Glu
            275                 280                 285

Asn Gly Asn Val Ser Arg Thr Glu Thr Ala Ser Thr Val Thr Glu Asn
            290                 295                 300

Lys Asp Gly Thr Tyr Asn Trp Met Ser Trp Leu Leu Val Asn Val Ser
305                 310                 315                 320

Ala His Arg Asp Asp Val Lys Leu Thr Cys Gln Val Glu His Asp Gly
            325                 330                 335

Gln Pro Ala Val Ser Lys Ser His Asp Leu Lys Val Ser Ala His Pro
            340                 345                 350

Lys Glu Gln Gly Ser Asn Thr Ala Ala Glu Asn Thr Gly Ser Asn Glu
            355                 360                 365

Arg Asn Ile Tyr Ile Val Val Gly Val Val Cys Thr Leu Leu Val Ala
            370                 375                 380

Leu Leu Met Ala Ala Leu Tyr Leu Val Arg Ile Arg Gln Lys Lys Ala
385                 390                 395                 400

Gln Gly Ser Thr Ser Ser Thr Arg Leu His Glu Pro Glu Lys Asn Ala
            405                 410                 415

Arg Glu Ile Thr Gln Asp Thr Asn Asp Ile Thr Tyr Ala Asp Leu Asn
            420                 425                 430

Leu Pro Lys Gly Lys Lys Pro Ala Pro Gln Ala Ala Glu Pro Asn Asn
            435                 440                 445

His Thr Glu Tyr Ala Ser Ile Gln Thr Ser Pro Gln Pro Ala Ser Glu
            450                 455                 460

Asp Thr Leu Thr Tyr Ala Asp Leu Asp Met Val His Leu Asn Arg Thr
465                 470                 475                 480

Pro Lys Gln Pro Ala Pro Lys Pro Glu Pro Ser Phe Ser Glu Tyr Ala
            485                 490                 495

Ser Val Gln Val Pro Arg Lys
            500

<210> SEQ ID NO 12
<211> LENGTH: 19
<212> TYPE: PRT
<213> ORGANISM: Homo sapiens

<400> SEQUENCE: 12

Arg Glu Leu Ile Tyr Asn Gln Lys Glu Gly His Phe Pro Arg Val Thr
1               5                   10                  15

Thr Val Ser

```
<210> SEQ ID NO 13
<211> LENGTH: 15
<212> TYPE: PRT
<213> ORGANISM: Homo sapiens

<400> SEQUENCE: 13

Val Thr Ser Leu Ile Pro Val Gly Pro Ile Gln Trp Phe Arg Gly
1               5                   10                  15

<210> SEQ ID NO 14
<211> LENGTH: 8
<212> TYPE: PRT
<213> ORGANISM: Homo sapiens

<400> SEQUENCE: 14

Val Lys Phe Arg Lys Gly Ser Pro
1               5

<210> SEQ ID NO 15
<211> LENGTH: 11
<212> TYPE: PRT
<213> ORGANISM: Homo sapiens

<400> SEQUENCE: 15

Ala Leu Asn Lys Ser Thr Val Pro Thr Asp Cys
1               5                   10

<210> SEQ ID NO 16
<211> LENGTH: 10
<212> TYPE: PRT
<213> ORGANISM: Homo sapiens

<400> SEQUENCE: 16

Ala Leu Asn Lys Ser Thr Val Pro Thr Asp
1               5                   10

<210> SEQ ID NO 17
<211> LENGTH: 10
<212> TYPE: PRT
<213> ORGANISM: Rattus norvegicus

<400> SEQUENCE: 17

Asn Asn Lys Ser Thr Thr Arg Glu Gln Asn
1               5                   10
```